United States Patent [19]
Sachinala et al.

[11] Patent Number: 5,571,907
[45] Date of Patent: Nov. 5, 1996

[54] EPOXY MONOMERS FROM SUCROSE

[75] Inventors: Navzer D. Sachinvala, Aiea, Hi.; Morton H. Litt, Cleveland, Ohio

[73] Assignee: Hawaiian Sugar Planters' Association, Aiea, Hi.

[21] Appl. No.: 388,569

[22] Filed: Feb. 14, 1995

Related U.S. Application Data

[63] Continuation-in-part of Ser. No. 199,695, Feb. 28, 1994, Pat. No. 5,470,931, which is a continuation-in-part of Ser. No. 28,545, Mar. 8, 1993, abandoned, which is a continuation-in-part of Ser. No. 877,813, May 4, 1992, Pat. No. 5,248,747, which is a continuation-in-part of Ser. No. 697,983, May 10, 1991, Pat. No. 5,116,961, which is a continuation-in-part of Ser. No. 623,548, Dec. 7, 1990, abandoned.

[51] Int. Cl.$^6$ ............................................. C07H 1/00
[52] U.S. Cl. .................. 536/120; 536/124; 549/525; 549/531; 527/300; 527/303; 527/312; 528/405; 528/406; 528/407
[58] Field of Search ........................ 536/120, 124; 549/525, 531

[56] References Cited

U.S. PATENT DOCUMENTS

| | | | |
|---|---|---|---|
| 2,492,169 | 12/1949 | Mast et al. | 575/354 |
| 2,539,706 | 1/1994 | Synder et al. | 526/216 |
| 2,606,881 | 8/1952 | Zief et al. | 526/238.21 |
| 3,915,921 | 10/1975 | Schlatzer, Jr. | 526/238.23 |
| 3,978,022 | 8/1976 | Carson | 524/392 |
| 4,026,908 | 5/1977 | Pralus et al. | 549/531 |
| 4,048,426 | 9/1977 | Solomon | 526/334 |
| 4,587,319 | 5/1986 | Tournier | 527/313 |
| 4,647,678 | 3/1987 | Eckwert et al. | 549/525 |
| 5,116,961 | 5/1992 | Sachinvala | 536/18.2 |
| 5,248,747 | 9/1993 | Sachinvala | 526/238.23 |
| 5,274,140 | 12/1993 | Venturello et al. | 549/531 |

FOREIGN PATENT DOCUMENTS

| | | |
|---|---|---|
| 000537660A | 4/1993 | European Pat. Off. |
| 03045604A2 | 2/1991 | Japan. |

OTHER PUBLICATIONS

I. C. McNeill, *Comprehensive Polymer Science*, I. C. McNeill, Ed., vol. 6, Pergamon Press, New York, pp. 451–500, 1989.

N. Grassie, *Chemistry of High Polymer Degradation Processes*. Interscience Publishers Inc., New York, 1956.

N. Grassie, A. Scotney, R. Jenkins, and T. I. Davis, *Chem. zvesti*, 26, 208 (1972).

N. Grassie and G. Scott, *Polymer Degradation & Stabilisation*, Cambridge University Press, London, pp. 1–67, 1985.

D. H. Solomon, *J. Macromol. Sci. Chem.*, A17, 337 (1982).

N. Grassie, *Pure & Appl. Chem.*, 30, 119 (1972).

N. Grassie and H. W. Melville, *Proc. Royal. Soc. Lond.*, A199, 14 (1949).

K. A. Holland and I. D. Rae, *Aust. J. Chem.*, 40. 687 (1987).

A. Meisters, G. Moad, E. Rizzardo, and D. H. Solomon, *Poly. Bull.* 20, 499 (1988).

T. Kashiwagi, A. Omori, and H. Nanbu, *Combustion and Flame*, 81, 188 (1990).

T. Kashiwagi, A. Inaba, J. E. Brown, K. Hatada, T. Kitayama and E. Masuda, *Macromolecules*, 19, 2160 (1986).

(List continued on next page.)

Primary Examiner—Mark Nagumo
Attorney, Agent, or Firm—Burns, Doane, Swecker & Mathis, L.L.P.

[57] ABSTRACT

A method for producing sucrose-based epoxy monomers having one to eight epoxy groups per molecule of sucrose, which comprises reacting a mixture comprising: a sucrose monomer having an allyl-containing group on at least one of the hydroxyl groups, and a reagent or catalyst selected from molybdenum, tungsten, vanadium, titanium and peracid, in the presence of hydrogen peroxide or a derivative thereof, in relative amounts sufficient to produce a sucrose-based epoxy monomer. Monomers thus produced are also provided. The sucrose-based epoxy monomers can be cured to produce a sucrose-based epoxy resin. Such resins are useful, for example, as adhesives, composites and coatings.

23 Claims, 12 Drawing Sheets

OTHER PUBLICATIONS

N. Grassie, A. Johnston, and A. Sctoney, *Eur. Polym. J.*, 17, 589 (1981).

N. Grassie, M.A.M. Diab, and A. Scotney, *Polym. Degradation Stab.*, 16, 19 (1986).

J. Popovic, Ch–H Song, L. Fischer, L. Katsikas, G. Hohne, J. Velickovic, and W. Schnabel, *Polym. Degradation Stab.*, 32, 265 (1991).

K. Hayakawa, K. Kawase, and H. Yamakita, *J. Appl. Polym. Sci.* 29, 4061 (1984).

J. San Roman, E. L. Madruga, and Y. J. Fontan, *Rev. Plast. Mod.*, 31, 213 (1976).

V. S. Nikiforenko, Yu S. Zaitsev, N. N. Alekseev, and O. I. Sholgon, *Plast. Massy*, 59, (1988).

F. M. Aliev and V. N. Zgonik, *Euro. Polym. J.*, 27, 969 (1991).

H. H. G. Jellinek, *Degradation of Vinyl Polymers*, Academic Press, New York, 74 1965.

I. C. McNeil, *Eur. Polym. J.*, 4, 21 (1968).

P. Cacioii, G. Moad, E. Rizzardo, A. K. Serelis and D. H. Solomon, *Polym. Bull. (Berlin)*, 11, 325 (1984).

A. Kaminska, H. Kaczmaerk, and S. Sanyal, *Polym. Networks Blends*, 1, 165 (1991).

A. Rincon, I. C. McNeil, *Polym. Degradation and Stab.*, 18, 99 (1987).

S. H. Goh, *Thermochimica Acta*, 153, 423 (1989).

N. D. Sachinvala, W. P. Niemczura, and M. H. Litt, *Carbohydr. Res.*, 218, 237 (1991).

Still et al., *Rapid Chromatographic Technique for Preparative Separations with Moderate Resolution*, J. Org. Chem., vol. 43, No. 14, 1978, pp. 2923–2925.

S. Steenken, H. P. Schuchmann, and C. von Sonntag, *The J. of Physical Chemistry*, 79, 763 (1975).

D. C. Nonabel, J. M. Tedder, and J. C. Walton, *Radicals*, Cambridge University Press, London, 1979, 55–61.

H. Zegota and C. von Sonntag, *Z. Naturforsch.*, 32b, 1060 (1977).

C. von Sonntag, M. Dizdaroglu, and D. Schulte–Frohlinde, *Z. Naturforsch.*, 31b, 857 (1976).

J. March, *Advanced Organic Chemistry*, 4th Edition, J. Wiley & Sons Inc., New York, pp. 1006–1010, 1992.

DKS International, Inc., *DK–Ester Sucrose Fatty Acid Ester*, Bulletin 1984.

Bobalek et al., *Preparation and Properties of Linoleate Esters of Sucrose*, I & EC Product Research and Development, Mar. 1963, vol. 2, No. 1, pp. 9–16.

J. K. Kochi, *Organometallic Mechanism and Catalysis*, Academic Press, NY 1978, pp. 346–349.

Osipow et al., *Methods of Preparation . . . Fatty Acid Esters of Sucrose*, Industrial and Engineering Chemistry, Sep. 1956, vol, 48, No. 9, pp. 1459–1462.

G. R. Ames, *Long–Chain Derivatives of Monosaccharides and Oligosaccharides*, Chemical Review, 1960, vol. 60, pp. 541–553.

Brimacombe et al., *Alkylation of Carbohydrates Using Sodium Hydride*, Carbohydrate Res., 2 (1966) pp. 167–169.

Peter Munk, J. Wiley, *Introduction to Macromolecular Science*, NY 1989, pp. 153–154.

G. Odian, 3rd Ed., J. Wiley, *Principles of Polymerization*, NY 1991, pp. 150–152.

Matsumoto et al., *Gelation in the Copolymerization of Methyl Methacrylate with Trimethylolpropane Trimethracylate*, European Polymer Journal, vol. 25, 1989, pp. 385–389.

Chemical Abstract 104(18): 150001f (Paus 1986).

Chemical Abstract 70(16): 68960p (Shafranskaya 1968).

Sachinvala et al., *Preparation of Poly(methyl methacrylate) and Copolymers Having Enhanced Thermal Stabilities Using Sucrose–Based Comonomers and Additives*, J. of Polymer Science: Part A, Polymer Chemistry, 1994, pp. 1–15.

March, J., *Advanced Organic Chemistry*, 4th Edition, J. Wiley & Sons Inc., New York, 1982, pp. 1006–1010.

Novichkou, L. M., *Izvestiya Acad. Sci.*, KAZ Sov. Soc. Rep. Chem. Ser.

Odian, G. *Principles of Polymerization*, 3rd edition, J. Wiley & Sons, New York, 1991, pp. 134–136.

J. March, Advanced Organic Chemistry, 4th Ed., Wiley, New York, 1992, 826–829.

R. H. Jacques et al., La Sucrere Belge, 95, 179–187, May, 1976.

R = H = mixed epoxy-allylsucroses 4
R = CH3 = mixed epoxy-crotylsucroses 5

R = H = octa-O-allylsucrose 2
R = CH3 = octa-O-crotylsucrose 3

Sucrose

R = R' = H = tri-O-(2',3'-epoxypropyl)-penta-O-methylsucrose 8
R = H, R' = CH3 = tri-O-(2',3'-epoxybutyl)-penta-O-methylsucrose 9

R = R' = H = tri-O-allyl-penta-O-methylsucrose 6
R = H, R' = CH3 = tri-O-crotyl-penta-O-methylsucrose 7

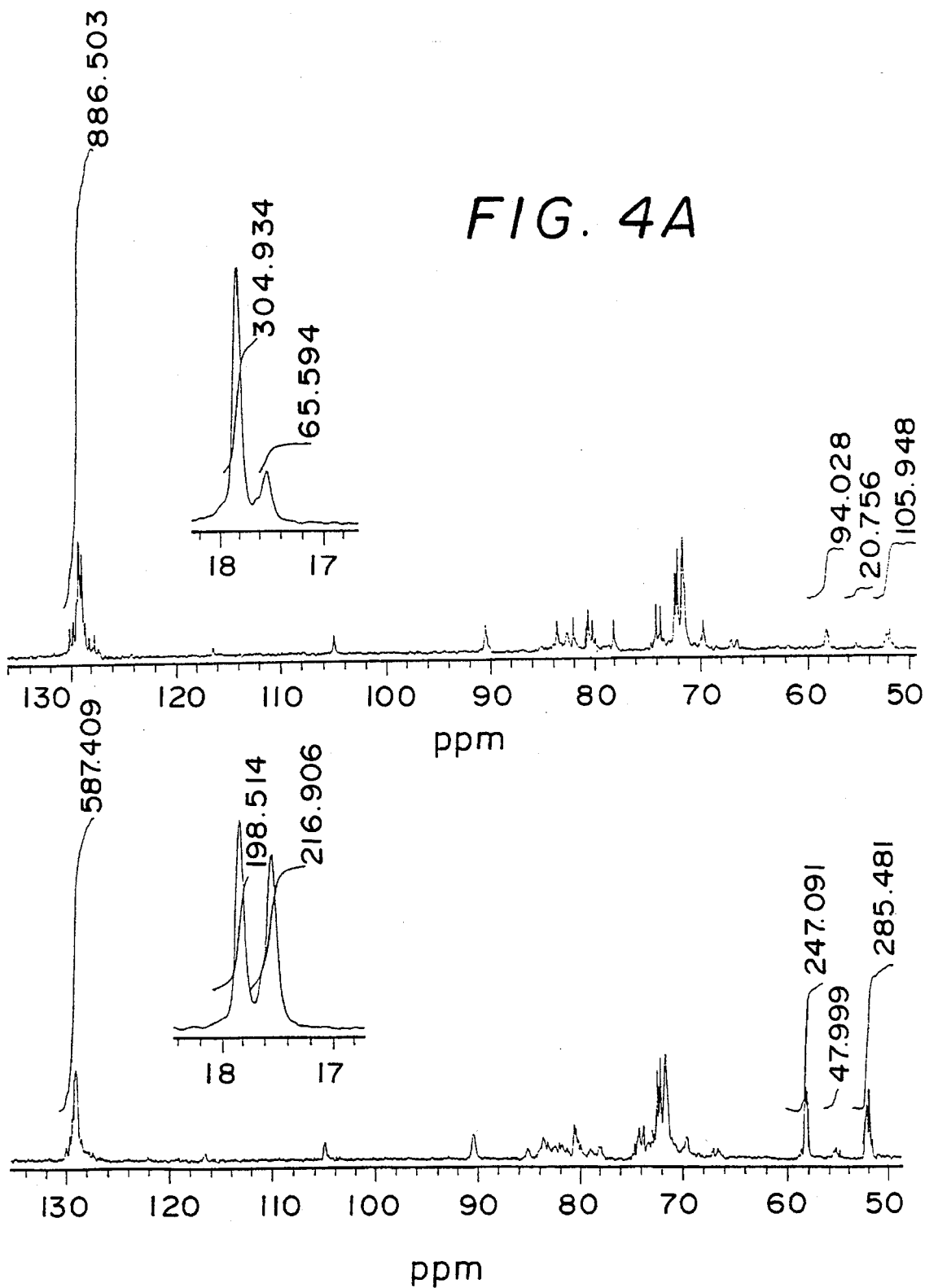

EPOXY MONOMERS FROM SUCROSE

GRANT REFERENCE

The invention described herein was partially funded by U.S.D.A. (A.R.S.) grant number 58-91H2-0-319.

RELATED APPLICATIONS

The present application is a continuation in part of U.S. Ser. No. 08/199,695, filed Feb. 28, 1994 now U.S. Pat. No. 5,470,931, which is a continuation in part of U.S. Ser. No. 08/028,545, filed Mar. 8, 1993 now abandoned, which is a continuation in part of 07/877,813, filed May 4, 1992, now U.S. Pat. No. 5,248,747, which is a continuation in part of U.S. application Ser. No. 07/697,983, filed May 10, 1991, now U.S. Pat. No. 5,116,961, which is a continuation in part of U.S. application Ser. No. 07/623,548, filed Dec. 7, 1990, now abandoned. These applications are incorporated by reference in their entirety herein.

BACKGROUND OF THE INVENTION

1. Field of The Invention

The subject invention relates to epoxy monomers suitable for the production of polymeric resins, methods for producing such epoxy monomers, and the resulting polymeric resins. The invention also generally relates to novel sucrose derivatives useful for preparing epoxy monomers and their polymerizable mixtures. Finally, the subject invention relates to articles coated with the epoxy resins, epoxy composites and the use of epoxy resins as adhesives.

2. Description of the Related Art

An epoxide, or oxirane, is a three membered ring (cyclic ether) containing two adjacent methylenes or methines and an oxygen. Epoxides are derivatives of ethylene oxide. Compounds containing epoxide groups are important because epoxides are highly reactive moieties that are useful starting materials for the synthetic chemist. In particular, epoxides are capable of being attacked by both electrophiles and nucleophiles. Epoxide chemistry is widely described in the literature such as in polymer chemistry texts and reviews (see, for example, Tanaka, Y. in *Epoxy Resins: Chemistry and Technology*, 2nd Edition, May, C. A. (editor), Marcel Dekker, New York. 1988, pp 9–284; Odian, G. *Principles of Polymerization*, 3rd Edition, J. Wiley & Sons, New York, 1991, pp 134–136; Stevens, M. P. *Polymer Chemistry*, 2nd Edition, Oxford University Press, New York, 1990, pp 329–351; and Bauer, R. S. in *Epoxy, Resins: Chemistry and Technology*, A.C.S. Audio Course, American Chemical Society, Washington, D. C., 1991).

Commercial epoxy resins are oligomeric materials that contain one or more epoxy or oxirane group per molecule. The most widely used epoxy resins are the diglycidyl ethers of bisphenol-A obtained upon reaction of bisphenol-A with epichlorohydrin (see, May, C. A. in *Epoxy Resins: Chemistry and Technology*, 2nd Edition, May, C. A. (editor), Marcel Dekker, 2nd Edition, New York, 1988, pp 1–8).

Since their introduction in the late forties, epoxy resins have permeated many technologies. They are used extensively in adhesives, reinforced materials, and as coatings. As adhesives, epoxy resins are used to bind glass, wood, metals, and plastic surfaces. As coatings, because of their chemical resistance and excellent corrosion protection, they are used as primers in the maintenance of off- and on-shore refineries, chemical plants, off-shore drilling platforms, ships, automobiles, appliances and aircrafts. They also line drums, pails, food and beverage containers since they are chemically inert, non-toxic and impart no taste when fully cured. In structural applications, epoxy resins find use in potting and encapsulation of electrical equipment; adhesives for automobile and aircraft manufacturing; sealants in flooring and paving applications; grouting agents; and reinforced composites for the construction of pipes, tanks, aircraft and automobile components. These structural applications are possible because epoxy resins set quickly and have solvent and chemical resistance; low shrinkage upon cure; and excellent electrical, thermal and moisture resistance. However, they have some special storage and handling requirements (see, May, C. A. in *Epoxy Resins: Chemistry and Technology*, 2nd Edition, May, C. A. (editor), Marcel Dekker, 2nd Edition, New York, 1988, pp 1–8).

The glass transition temperature for epoxy resins cured with most standard curing agents tends to be low. This limits their usefulness in many applications. In addition, their manufacturing costs are high when compared with other crosslinked systems such as polyurethanes, phenol formaldehyde resins, urea formaldehyde resins and crosslinked polyesters. Therefore, there exists a need in the art for improved epoxy monomers which can be used for preparing epoxy polymers and resins. Moreover, given the various uses for epoxy polymers and resins, it is clear that improved epoxide monomers and polymers with better physical properties resulting from these methods are highly desirable. In addition to improved methods for producing epoxy monomers and polymers inexpensively, improved coated products, composites and adhesives comprising such epoxy monomers and polymers resulting from these methods would be highly desirable.

OBJECTS AND SUMMARY OF THE INVENTION

It is an object of this invention to avoid or alleviate the problems of the prior art.

In its broadest embodiment it is an object of this invention to provide polymers exhibiting improved thermal stability and a method for their production. It is a particular object of the invention to produce polymers having enhanced thermal stability by polymerizing: an allyl ether-containing monomer (preferably having 3–20 carbon atoms in its skeleton) which is bonded to at least one primary or secondary hydroxyl group on a saccharide; and one or more monomers selected from the group consisting of methacrylate esters, acrylate esters, acrylamides, styrene and acrylate monomers; wherein the relative amounts thereof and conditions are effective to produce polymers exhibiting enhanced thermal stabilities.

The allyl ether or allyl ether groups will generally have an unsaturation beta to the ether oxygen.

It is another object of the invention to provide polymers exhibiting enhanced thermal stability and a method for their production by polymerizing a mixture comprising: a monomer comprising allyl-containing ethers (wherein the allyl-containing group preferably has 3–20 carbon atoms in its skeleton) of a monosaccharide, disaccharide, oligosaccharide, polysaccharide or heteropolysaccharide; and one or more monomers selected from the group consisting of methacrylate ester monomers, acrylate ester monomers, acrylamide monomers and styrene monomers, wherein the relative amounts thereof and conditions are effective to produce polymers exhibiting enhanced thermal stabilities.

It is another object of this invention to provide stable polymers and a method for their production by polymerizing a mixture comprising: a benzylether compound or benzylether compound comprising long chain hydrocarbon substituents at one or more of positions 2 to 6 of the aromatic ring, wherein preferably the hydrocarbon comprises about 3 to 20 carbon atoms; and one or more monomers selected from methacrylate esters, acrylamides, styrene monomers and acrylate esters, wherein the relative amounts thereof and polymerization conditions are effective to produce polymers exhibiting enhanced thermal stabilities.

It is yet another object of the invention to provide polymers exhibiting enhanced thermal stabilities and a method for their production by polymerizing a mixture comprising: an allyl ether-containing monomer, preferably having about 3 to 20 carbon atoms and containing more than one double bond in its skeleton; and one or more monomers selected, e.g., from methacrylate esters, acrylate esters, acrylamides and styrene monomers, wherein the relative amounts thereof and polymerization conditions are effective to produce polymers exhibiting enhanced thermal stabilities.

More specifically, it is an object of the invention to provide improved methods for producing stabilized polymers using a saccharide monomer, preferably a sucrose monomer having an allyl-containing group on at least one of the hydroxyl groups. The allyl-containing group on the hydroxyl groups of the sucrose monomer is preferably a long chain ($C_3$–$C_{20}$) allyl-containing ether. The long chain ($C_3$–$C_{20}$) allyl ether may contain more than one double bond in the carbon chain.

It is a specific object of the invention to provide improved methods for producing stabilized polymers comprising methacrylate ester, acrylate ester, acrylamide or styrene monomers using a saccharide monomer, e.g., a sucrose-based monomer containing an unsaturation selected from 1',6,6'-trimethacryloyl-2,3,3',4,4'-penta-O-methylsucrose, 1',2,3,3',4,4',6,6'-octa-O-allylsucrose or 1',2,3,3',4,4',6,6'-octa-O-crotyl sucrose as a stabilization agent.

It is another object of the invention to provide improved polymers using as a stabilization agent a saccharide monomer, in particular a sucrose-based monomer having an allyl-containing group on at least one of the hydroxyl groups, preferably a long chain ($C_3$–$C_{20}$) allyl-containing ether group on the hydroxyl group, and more preferably, the long chain ($C_3$–$C_{20}$) allyl-containing ether having more than one double bond in the carbon chain.

It is still another object of the invention to provide improved stabilized polymers comprising methacrylate ester, acrylate ester, acrylamide or styrene monomers using a saccharide monomer, in particular a sucrose-based monomer having an allyl-containing group selected from 1',2,3,3',4,4',6,6'-octa-O-allylsucrose and 1',2,3,3',4,4',6,6'-octa-O-crotylsucrose as a stabilization agent.

It is another object of the invention to provide polymerizable mixtures which upon polymerization result in polymers having enhanced thermal stability, which mixtures comprise a sucrose-based monomer as a stabilization agent having an allyl-containing group on at least one of the hydroxyl groups, preferably a long chain ($C_3$–$C_{20}$) allyl ether-containing group on the hydroxyl group, and more preferably, the long chain ($C_3$–$C_{20}$) allyl-containing ether having more than one double bond in the carbon chain, a monomer which reacts therewith, and optionally a free radical initiator in amounts sufficient to facilitate polymerization.

It is a further object of the invention to provide polymerizable mixtures which upon polymerization result in stabilized polymers having enhanced thermal stability, which mixtures comprise a sucrose-based monomer having an allyl-containing group selected from 1',2,3,3',4,4',6,6'-octa-O-allylsucrose and 1',2,3,3',4,4',6,6'-octa-O-crotylsucrose as a stabilization agent, a methacrylate ester, acrylate ester, acrylamide or styrene monomer and optionally a free radical initiator in relative amounts sufficient to facilitate polymerization and the production of polymers having enhanced thermal stability.

It is still another object of the invention to provide polymers having enhanced thermal stability by polymerizing acrylic esters O-methylated saccharides and one or more monomers selected from the group consisting of methacrylate esters, acrylate esters, acrylamides and styrene monomers; wherein the relative amounts thereof and conditions are effective to produce polymers exhibiting enhanced thermal stabilities.

It is a specific object of the invention to provide improved methods for producing stabilized polymers comprising methacrylate ester, acrylate ester, acrylamide or styrene monomers using a saccharide monomer, e.g., a sucrose-based monomer containing an acrylic ester, such as 1',6,6'-trimethacryloyl-2,3,3',4,4'-penta-O-methylsucrose.

It is still another object of the invention to provide improved methods for producing non-crosslinked polymers using a non-crosslinking sucrose-based compound or monomer.

It is still a further object of the invention to provide improved methods for producing non-crosslinked polymers comprising methacrylate ester, acrylate ester, acrylamide or styrene monomers using a non-crosslinking sucrose-based additive selected from octa-O-crotyl sucrose, octa-O-methylsucrose, other octa-O-alkylsucroses or partially substituted O-alkyl and O-crotyl sucrose derivatives.

It is another object of the invention to provide improved uncrosslinked thermoplastic polymers using non-crosslinking saccharide-based monomers or additives.

It is a further object of the invention to provide improved uncrosslinked thermoplastic polymers comprising methacrylate ester, acrylate ester, acrylamide or styrene monomers using a non-crosslinking saccharide-based monomer selected from octa-O-crotylsucrose, octa-O-methylsucrose, other octa-O-alkylsucroses, or partially substituted O-methyl, O-crotyl or O-alkyl sucrose derivatives.

It is still another object of the invention to provide polymerizable mixtures which upon polymerization result in non-crosslinked polymers having enhanced thermal stability, which mixtures comprise a non-crosslinking sucrose-based monomer or compound, a monomer which reacts therewith, and optionally a free radical initiator in amounts sufficient to facilitate polymerization.

It is still a further object of the invention to provide polymerizable mixtures which upon polymerization result in non-crosslinked polymers having enhanced thermal stability, which mixtures comprise a non-crosslinking saccharide-based monomer or compound selected from octa-O-crotylsucrose, octa-O-methylsucrose, other octa-O-alkylsucroses, or partially substituted O-methyl, O-crotyl, or O-alkyl sucrose derivatives, a monomer which reacts therewith selected from methacrylate ester, acrylate ester, acrylamide or styrene monomers, and optionally a free radical initiator in amounts sufficient to facilitate polymerization.

It is still further an object of the invention to provide a novel sucrose derivative, 1',2,3,3',4,4',6,6'-octa-O-crotylsucrose, and a method of making it. This novel sucrose derivative is useful in providing uncrosslinked polymers exhibiting enhanced thermal stabilities.

It is still further an object of the invention to provide improved methods for producing stabilized polymers comprising methacrylate ester, acrylate ester, acrylamide or styrene monomers using 1',2,3,3',4,4',6,6'-octa-O-crotylsucrose.

It is still further an object of the invention to provide improved stabilized polymers using 1',2,3,3',4,4',6,6'-octa-O-crotylsucrose as a stabilizing agent.

The present inventors have surprisingly discovered that not only do the subject sucrose-based stabilizing agents outperform any existing acrylate, methacrylate or acrylamide crosslinker in terms of their efficiency (N. Sachinvala, M. Lilt, R. F. Ju, U.S. Pat. No. 5,248,747), but that the sucrose-based stabilization agents provide unprecedented thermal stability to methyl methacrylate and styrene copolymers, among others. The present inventors have confirmed the enhanced thermal stability provided by sucrose-based stabilization agents by: (1) showing the thermal degradation temperatures, glass transition temperatures, and polymer aging studies on poly(methyl methacrylate) copolymers containing crosslinkers 1',6,6'-trimethacryloyl-2,3,3'4,4'-penta-O-methylsucrose and 1',2,3,3',4,4',6,6'-octa-O-allylsucrose, additive 1',2,3,3',4,4',6,6'-octa-O-methylsucrose, and non-crosslinking stabilizer 1',2,3,3',4,4',6,6'-octa-O-crotyl sucrose; (2) comparing sucrose-based copolymers directly with methyl methacrylate polymers containing the crosslinker trimethylopropane trimethacrylate; and (3) comparing sucrose-based copolymers with commercial samples of polymers prepared by Du Pont (Lucite®), Rohm & Haas (Plexiglas®), K.S.H. Inc., and Cyro (Acrylite®).

Given the enhanced thermal stability and physical properties inherent to the polymers of the invention, these polymers should have particular applicability in fire retardant compositions, and in the preparation of articles and compositions which may be subjected to elevated temperatures.

In at least 1',6,6'-trimethacryloyl-2,3,3'4,4'-penta-O-methylsucrose, it is believed that this enhanced crosslinking efficiency occurs at least in part because of the relatively large atom separation between the reactive sites in the crosslinking monomer. For example, in the 1',6,6'-trimethacryloyl-2,3,3'4,4'-penta-O-methylsucrose molecule, the distance between the reactive sites of the 6 and 6' methacryloyl moieties is 16 atoms, the distance between the reactive ends at the 1' and 6' positions is 12 atoms and in addition these two positions are anti in orientation with respect to each other on the fructopyranosyl moiety, the distance between the reactive ends at the 1' and 6 positions is 14 atoms and there is an intervening 2,3,4'-tri-O-methyl-glucopyranosyl moiety. However, the present inventors do not restrict themselves to their belief as to the mechanism by which this or other enhanced thermally stable polymers are obtained in the present invention.

As to both those sucrose-based monomers of the present invention which do not function as crosslinking agents as well as those which do function as crosslinking agents, it is also believed that thermal stability is afforded to polymers containing the sucrose-based alkyl, allyl and crotyl ethers of the present invention due to the ability of these ethers to chain transfer with radicals at elevated temperatures. The normal result of chain transfer at the above-mentioned sucrose ethers is fragmentation to generate alkyl, allyl or crotyl radicals (see, S. Steenken et al, *The J. of Physical Chemistry*, 79, 763 (1975); D.C. Nonebel et al, *Radicals*, Cambridge University Press, London, 1979; H. Zegota et al, *Z. Naturforsch.*, 32b, 1060 (1977); C. von Sonntag et al, *Z. Naturforsch.*, 31b, 857 (1976)) (See FIG. 3). Chain transfer to additive during polymerization will increase the final thermal stability of the polymer, because most polymer chains are terminated with hydrogen (FIG. 1). However, it is believed that there will always be some weak links formed during radical termination. Molecules with such weak links will start depropagating at relatively low temperatures. Chain transferred polymers are more stable than pure polymers. The stability is enhanced by further chain transfer of the depropagating radical on the sucrose moiety. The resulting small radical fragment can then terminate a second depropagating chain. With the allyl-containing compounds of the present invention, copolymerization of allyl and crotyl groups provides additional stability since depropagation will stop when an allyl or crotyl moiety in the chain is reached. This radical will either terminate or chain transfer.

Although not wishing to be bound by any theory, the mechanism of stability that is believed to be operating is as follows: saccharide ethers having many tertiary hydrogens alpha to oxygen are relatively stable to chain transfer at normal polymerization temperatures. At temperatures where the polymer is unstable, these hydrogens chain transfer with radicals and fragment to produce small alkyl, allyl or crotyl radicals which can combine with and terminate the depropagating chain. Thus, the sucrose-ether derivatives quench depropagation reactions.

Therefore, the use of sucrose-based monomers having an allyl-containing group on at least one of the hydroxyl groups, preferably a long chain ($C_3$–$C_{20}$) allyl-containing ether group on the hydroxyl group, and more preferably, the long chain ($C_3$–$C_{20}$) allyl-containing ether having more than one double bond in the carbon chain, should result in improved methods of stabilizing monomers, in particular methacrylate esters, acrylate esters, acrylamide and styrene monomers, and should also result in crosslinked or non-crosslinked polymers having enhanced thermal stability and enhanced mechanical properties.

In another aspect of the present invention, the use of 1',6,6'-trimethacryloyl-2,3,3'4,4'-penta-O-methylsucrose results in improved methods of stabilizing monomers.

In another aspect of the present invention, the present inventors have also discovered that the addition of non-crosslinking sucrose based materials, for example the additive 1',2,3,3',4,4',6,6'-octa-O-methylsucrose, under low temperature polymerization conditions, provides more thermal stability to a methyl methacrylate polymer than the crosslinker trimethylolpropane trimethacrylate and parallels the thermal stability of extruded high molecular weight methyl methacrylate polymers.

Therefore, the use of non-crosslinking sucrose-based additives should result in improved methods of producing a non-crosslinked polymer, in particular a non-crosslinked polymer comprised of methacrylate esters, acrylate esters, acrylamides or styrene monomers, and should result in non-crosslinked polymers having enhanced thermal stability.

In general, it is an object of the present invention to provide sucrose-based epoxy monomers of the novel sucrose derivatives identified herein.

It is a specific object of the invention to partially or completely epoxidize the $C_3$–$C_{20}$ allyl-containing groups on octa-O-allylsucrose or octa-O-crotylsucrose to generate epoxy-O-allyl or epoxy-O-crotyl derivatives of sucrose and to use these sucrose-based epoxy monomers for the production of epoxy adhesives, paints, moldings, castings and coatings.

In another aspect of the present invention, octa-O-allyl- and octa-O-crotylsucrose monomers are transformed in one step to a series of epoxy monomers comprising one to eight epoxy groups per sucrose.

A further aspect of the present invention is a method for producing a saccharide-based epoxy monomer having one to eight epoxy groups per molecule of sucrose, which comprises reacting a mixture comprising: a monomer comprising an allyl ether-containing group which is bonded to at least one primary or secondary hydroxyl group on a saccharide; and an enzyme, acidic or metallic reagent or catalyst in the presence of an oxidizing agent, in relative amounts sufficient to produce a saccharide-based epoxy monomer having one to eight epoxy groups per molecule of sucrose.

The allyl-containing group is preferably an allyl-containing ether comprising from about 3 to 20 carbon atoms in its skeleton, preferably having unsaturation beta to the ether group. A more preferred structure comprises an allyl ether-containing group having more than one double bond.

In such a method, useful catalysts include peracids and traditional molybdenum, tungsten and vanadium catalysts.

A still further aspect of the present invention is a method for producing sucrose-based epoxy monomers having one to seven epoxy groups per molecule of sucrose, which comprises reacting a mixture comprising: a monomer comprising an allyl-containing group which is bonded to at least one primary or secondary hydroxyl group on a sucrose and an acidic or metallic catalyst in the presence of an oxidizing agent, in relative amounts sufficient to produce a sucrose-based epoxy monomer having one to seven epoxy groups per molecule of sucrose.

Preferably, the allyl-containing group of the sucrose monomer is a $C_3$–$C_{20}$ allyl-containing ether. More preferred is a $C_3$–$C_{20}$ allyl-containing ether that may contain more than one double bond.

Preferred oxidizing agents include hydrogen peroxide, t-butyl hydroperoxide, cumene hydroperoxide, metachloroperoxy benzoic acid, peracetic acid or a derivative thereof.

Monomers produced by the above methods are an additional aspect of the present invention.

Further, the present invention provides a method for producing a crosslinked resin, which comprises reacting a mixture comprising: sucrose-based epoxy monomers having one to six epoxy groups per molecule of sucrose; and a curing agent, in relative amounts sufficient to produce a sucrose-based crosslinked resin.

In such methods, the curing agent may be a nucleophilic curing agent or an electrophilic curing agent.

In another aspect of the present invention, sucrose-based epoxy monomers are used to produce epoxy resins. In such resins, the sucrose-based epoxy monomers may comprise more than 50% of the weight of the polymer. Furthermore, sucrose-based epoxy resins may be copolymerized with known epoxy materials to generate resins with less than 50% by weight of the sucrose-based materials.

In another aspect of the present invention, the crosslinked resin produced by such methods are provided.

A still further aspect of the present invention is the epoxy-allylsucrose or epoxy-crotylsucrose monomer thus produced.

In a still further aspect, the present invention provides a method for preparing an epoxy-allylsucrose or epoxy-crotylsucrose monomer comprising: treating a dimethylacetamide or dimethylsulfoxide solution of sucrose with a suspension of dimethylsulfoxide and sodium hydride at a temperature of between about 0° C. and about 10° C. to obtain a sucrose mixture; stirring the sucrose mixture for between about 30 and about 80 minutes while allowing the temperature to attain between about 35 to about 40 degrees C; and stirring the mixture for about 60 minutes at that temperature. The method further comprises cooling the sucrose mixture to between about 0 and about 10 degrees C; treating the sucrose mixture with allyl bromide or crotyl chloride. Following addition at 10° C., the temperature of the reaction mixture was monitored internally and the mixture allowed to attain 40° C., and stirred overnight. The resulting yellow mixture was cooled to 10° C. and quenched with 5% aqueous sodium hydroxide, diluted with water and extracted with ethyl acetate. The organic extracts were combined, washed serially with water and brine dried over anhydrous sodium sulfate, filtered through charcoal and then concentrated in vacuo. Flash column chromatography of the residue, on a silica gel column using hexanes and 10% ethylacetate in hexanes provided the desired products.

Preferably, dimethylacetamide or dimethylsulfoxide solution of sucrose (5 g, 14.62 mmol in 30 mL solvent) is treated with a suspension of dimethylsulfoxide (300 mL) and sodium hydride (60% in oil, 8.4 g, 210 mmol, washed 4×15 mL with dry hexanes) to obtain a sucrose mixture. In addition, the sucrose mixture with allyl bromide (13 mL, 150.22 mmol, added over 30 minutes) or crotyl chloride (14.63 mL, 50 mmol, added over 30 minutes). Further, the cooled was quenched with 5% aqueous sodium hydroxide (30 mL), diluted with water (500 mL) and extracted with ethyl acetate (4×100 mL). The organic extracts were combined, washed serially with water and brine (3×150 mL each) dried over anhydrous sodium sulfate, filtered through charcoal and then concentrated in vacuo. Still further, flash column chromatography of the residue on a silica gel (230–440 mesh) column (7×15 cm) using hexanes and 10% ethylacetate in hexanes (3 L) provided the desired products in 87–90% yields. These preferred amounts are relative amounts only and may be proportionately altered in practicing the invention. The invention should not be limited by the given exemplary amounts.

In another aspect, the use of sucrose based epoxy resins of the present invention results in improved adhesives, reinforced materials and coatings. Such adhesives, reinforced materials and coatings are particularly advantageous because epoxy resins set quickly and have solvent and chemical resistance; low shrinkage upon cure; and excellent electrical, thermal and moisture resistance. Particularly improved properties are achieved when the epoxy resins are applied, for example to glass, wood, steel and aluminum surfaces, as well as other surfaces requiring adhesives, reinforced materials and coatings.

A. The peaks at $\delta 129$ ppm correspond to the olefinic carbons of the crotyl group, and the peaks of $\delta 52$–58 ppm correspond to the epoxy carbons. The amount of epoxy crotyl sucrose was calculated by dividing the sum of the integrals of the epoxy carbons by the total integral value of the olefin+epoxy carbons; in this case the product contained two epoxy groups per sucrose. Similarly, the insert shows the methyl peak of the unepoxidized crotyl group at 17.8 ppm and the methyl peak of the epoxidized crotyl group at 17.5 ppm. Here too the integral ratio confirms two epoxy groups per sucrose.

B. The spectrum shows an increase in the amount of epoxidized crotyl sucroses with increasing amounts of peracetic acid. The size of the epoxide peaks at the 52–58 ppm region and at 17.5 ppm increased, showing four epoxy groups per sucrose.

C. The spectrum shows residual traces of olefin. The number of epoxy groups per sucrose was determined to be seven.

containing group on at least one of the hydroxyl groups, preferably a long chain ($C_3$–$C_{20}$) allyl-containing ether group on the hydroxyl group, and more preferably a long chain ($C_3$–$C_{20}$) allyl-containing ether having more than one double bond in the carbon chain. Preferred stabilization agents include 1',2,3,3',4,4',6,6'-octa-O-allylsucrose and 1',2,3,3',4,4',6,6'-octa-O-crotylsucrose.

In another embodiment, the stabilization agent is an acrylic ester derivative of sucrose. Preferably the acrylic ester is 1',6,6'-trimethacryloyl-2,3,3',4,4'-penta-O-methylsucrose. 1',6,6'-trimethacryloyl-2,3,3',4,4'-penta-O-methylsucrose comprises the following structure:

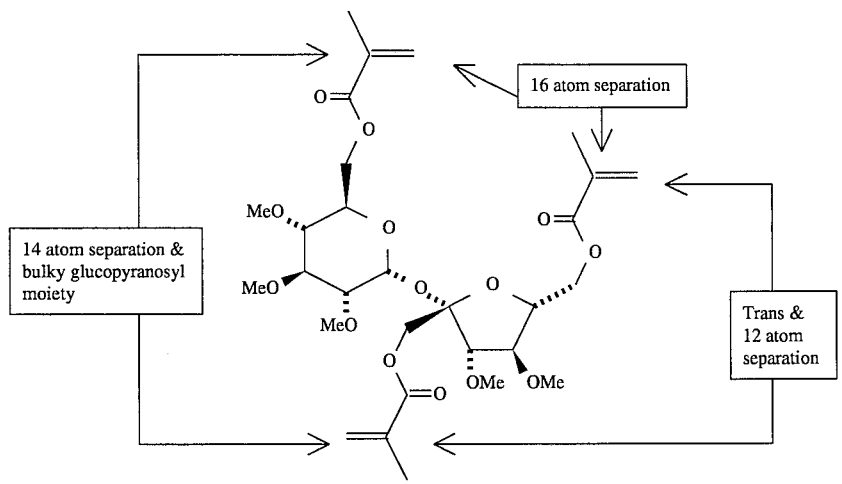

Figure 5:
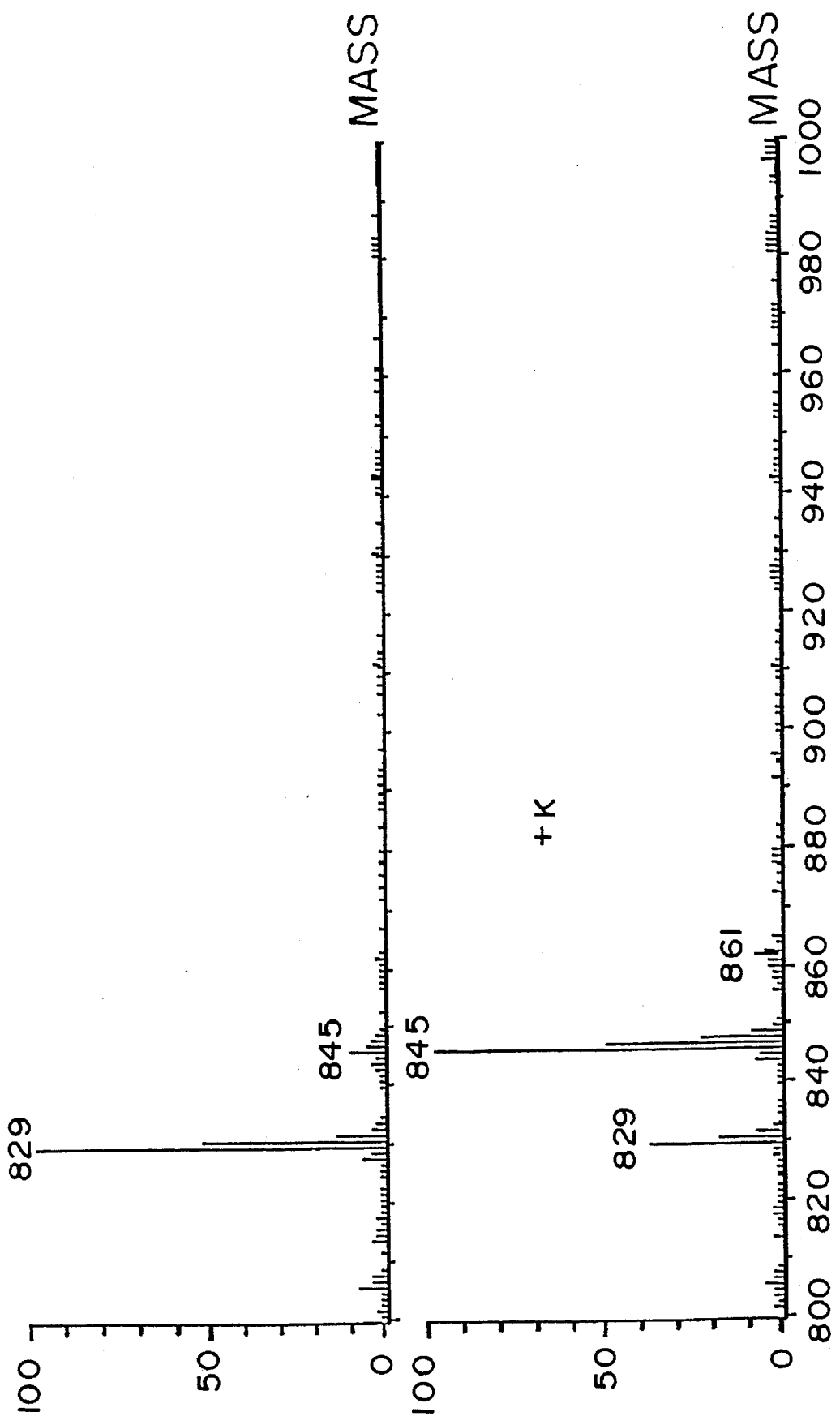

FIG. 5 illustrates mass spectra of epoxy crotyl sucrose containing two epoxy groups for sucrose.

Figure 6:
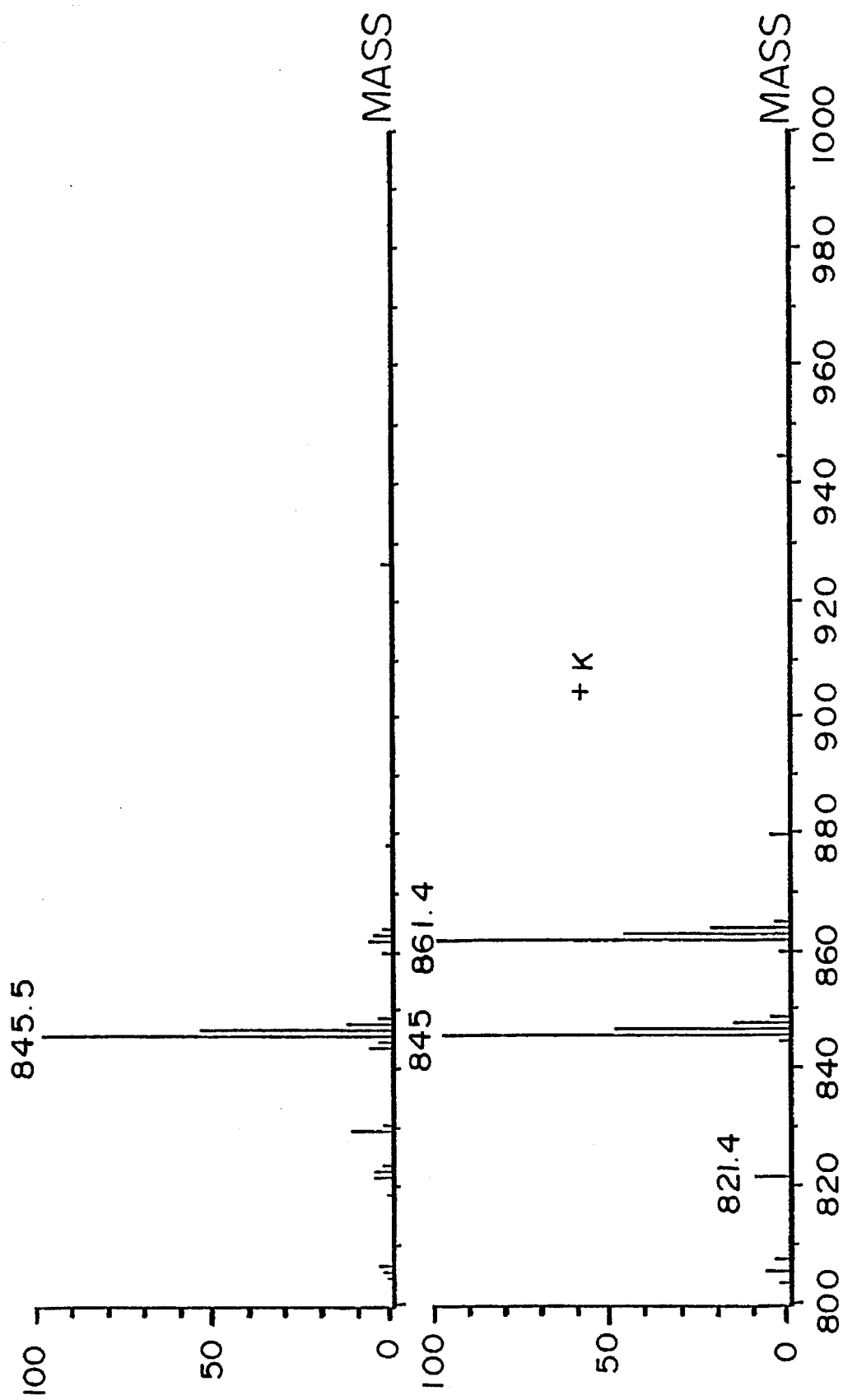

FIG. 6 shows mass spectra of epoxy crotyl sucrose containing three epoxy groups per sucrose.

Figure 7:
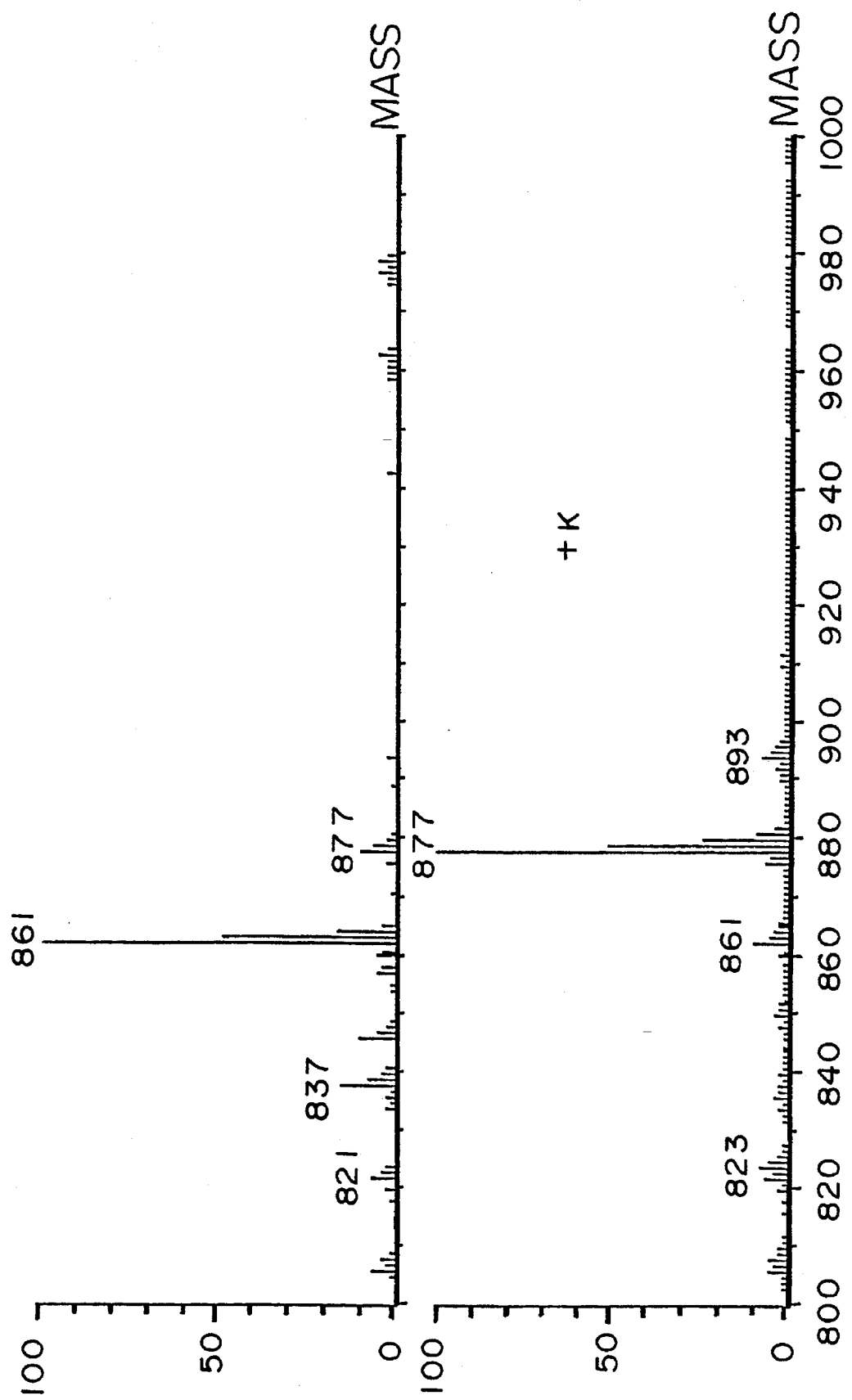

FIG. 7 illustrates mass spectra of epoxy crotyl sucrose containing four epoxy groups per sucrose.

Figure 8:
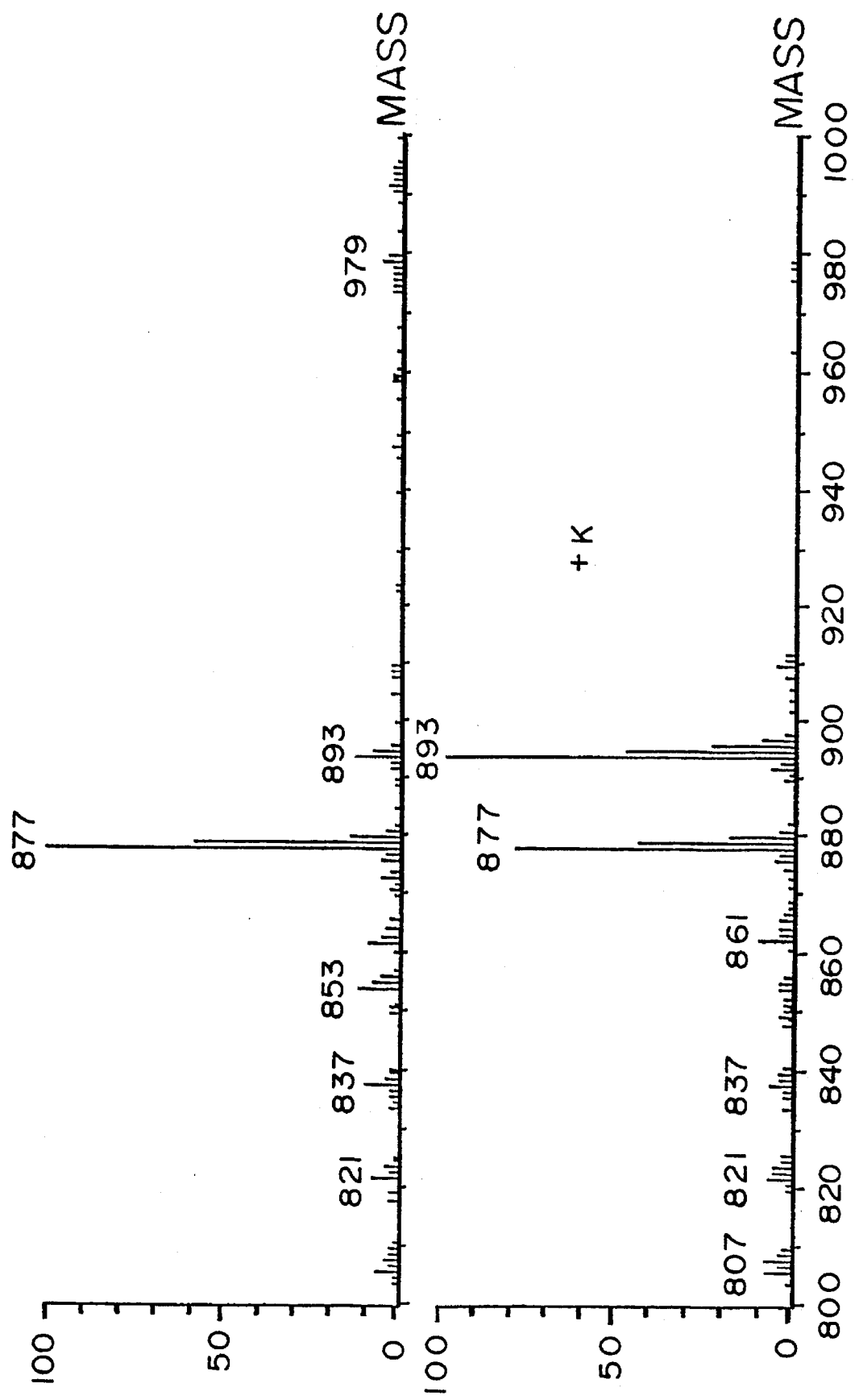

FIG. 8 shows mass spectra of epoxy crotyl sucrose containing five epoxy groups per sucrose.

Figure 9:
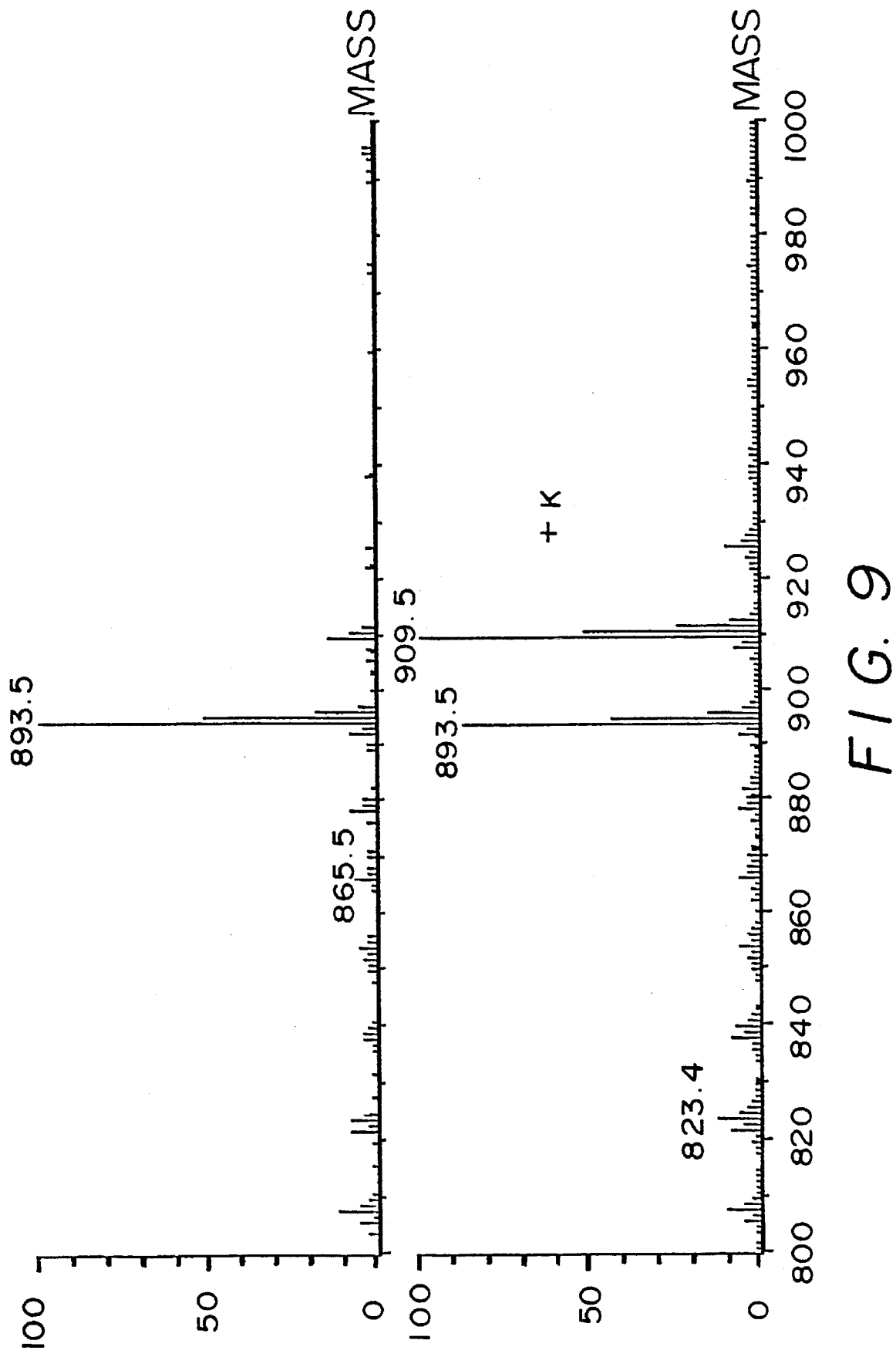

FIG. 9 shows mass spectra of epoxy crotyl sucrose containing six epoxy groups per sucrose.

Figure 10:
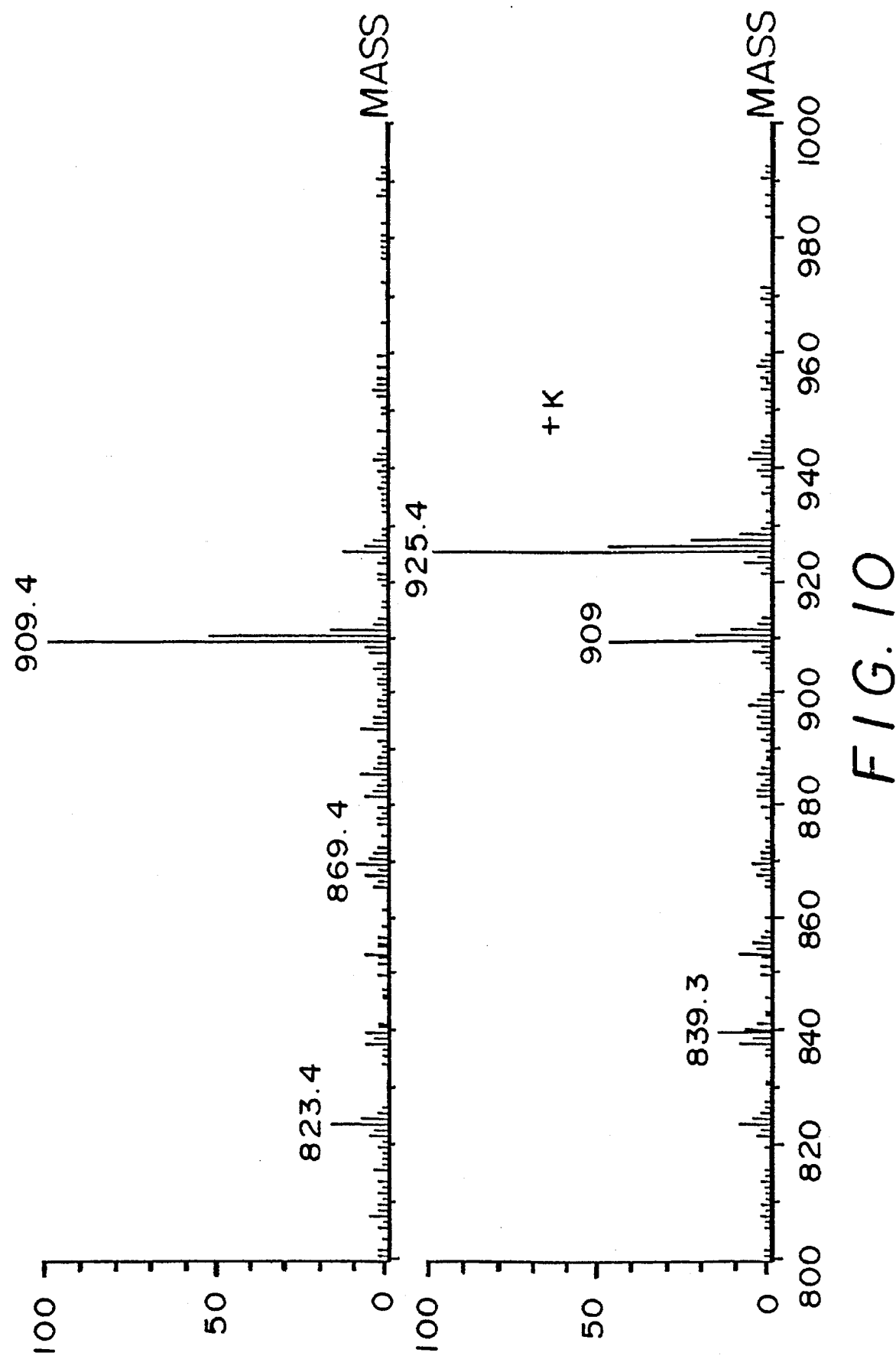

FIG. 10 illustrates mass spectra of epoxy crotyl sucrose containing seven epoxy groups per sucrose.

Figure 11:
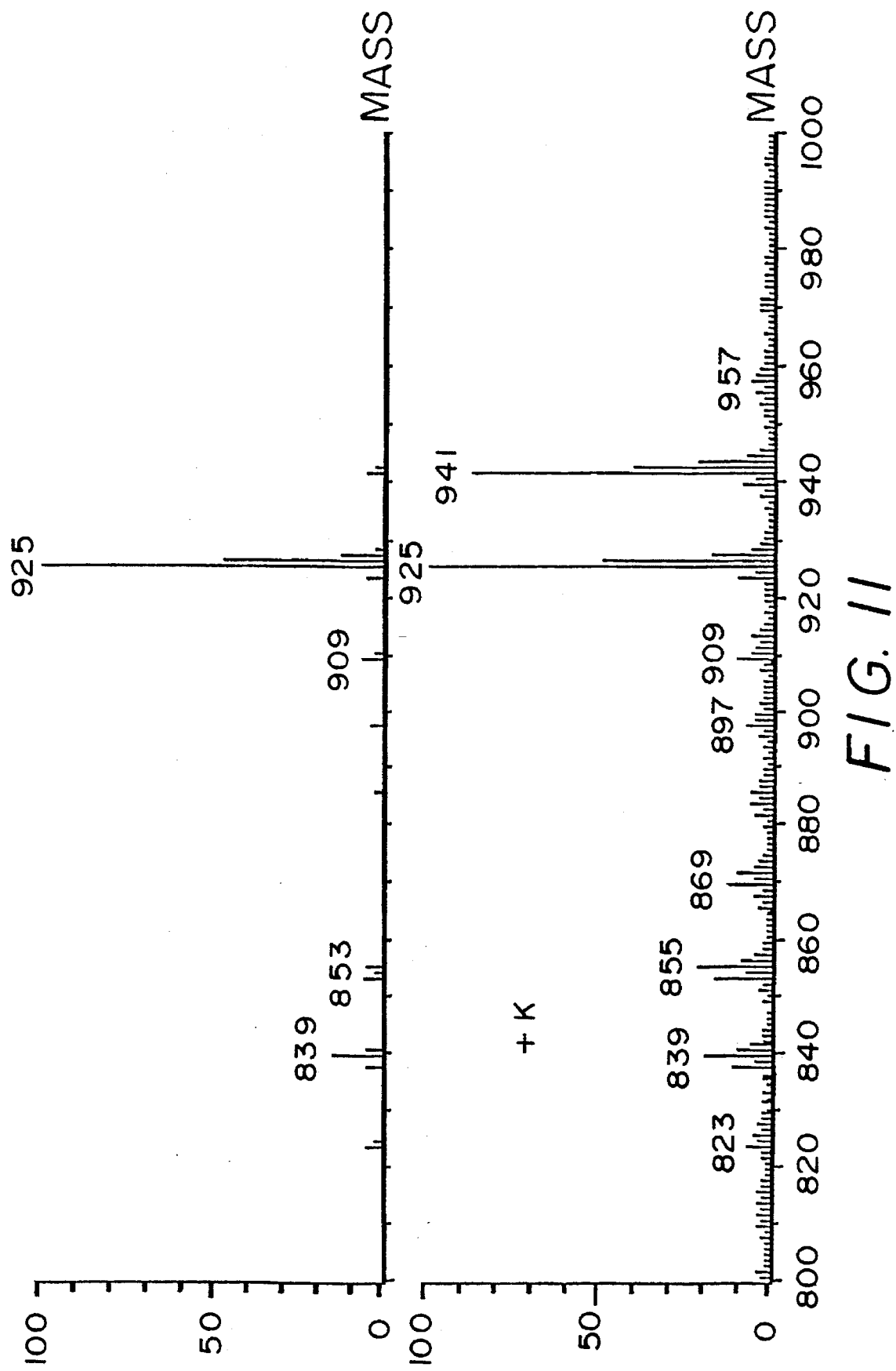

FIG. 11 shows mass spectra of epoxy crotyl sucrose containing eight epoxy groups per sucrose.

DETAILED DESCRIPTION OF THE PREFERRED EMBODIMENTS

As discussed above, the subject invention in one of its preferred embodiments relates to methods of using sucrose-based monomers having an allyl-containing group on at least one of the hydroxyl groups, preferably a long chain ($C_3$–$C_{20}$) allyl-containing ether group on the hydroxyl group, and more preferably, the long chain ($C_3$–$C_{20}$) allyl-containing ether having more than one double bond in the carbon chain, as a novel stabilization agent in polymerization processes, and polymers obtained using this stabilization agent having enhanced thermal stability. The stabilization agent is a sucrose-based monomer having an allyl- As can be seen from the structure, inherent in the design of 1',6,6'-trimethacryloyl-2,3,3'4,4'-penta-O-methylsucrose are two structural features that are believed to account for its increased crosslinking efficiency (cf. U.S. Pat. No. 5,248,747) and for the thermal stability this crosslinker affords its copolymers.

First, as explained previously in U.S. Pat. No. 5,248,747 the enhanced crosslinking efficiency of 1',6,6'-trimethacryloyl-2,3,3'4,4'-penta-O-methylsucrose may be attributed to the fact that it is only remotely possible for any two reactive ends of the methacryloyl groups in this crosslinker to coalesce intramolecularly in the presence of excess of the monomer to be polymerized. As can be seen in the above structure, a 16-atom separation exists between the reactive ends of the methacryloyl moieties at the 6 and 6' positions; a 12-atom distance exists between the 1' and 6' methacryloyl moieties, and these groups are anti to each other; and a 14-atom distance exists between the methacryloyl groups at the 1' and 6 ends, and they contain the bulky 2,3,4-tri-O-methylglucopyranosyl group between them.

In these materials, a cleaved chain may still be bound somewhere and may not be free to escape the matrix of the copolymer. Subsequent reunion of the cleaved chains may give rise to additional networks. This may not be the case in thermoset copolymers that contain TMPTMA as the crosslinking agent. Since the crosslinking efficiency of TMPTMA is very low, chains may be completely severed and free to fly away. Equilibrium swelling studies on crosslinked polymers show that this sucrose-based methacrylate crosslinker is 30 to 40% more efficient than commercial trimethacrylate crosslinkers.

Additionally, the methyl groups in 1',6,6'-trimethacryloyl-2,3,3'4,4'-penta-O-methylsucrose are unaffected by heat (provided no acids or nucleophiles are present in the depolymerizing milieu) which contributes to the increased thermal stability of copolymers containing 1',6,6'-trimethacryloyl-2,3,3'4,4'-penta- O-methylsucrose as the stabilizing agent. Moreover, radical cleavage of the disaccharides and hydrogen abstraction for carbons bearing ether groups are believed to yield fragments by chain transfer processes which may rejoin to create further crosslinks.

1',2,3,3',4,4',6,6'-octa-O-allylsucrose is a more economical sucrose derivative which may also be used as a stabilizing agent in order to enhance the thermal properties of the resulting polymer. Its structure is as follows:

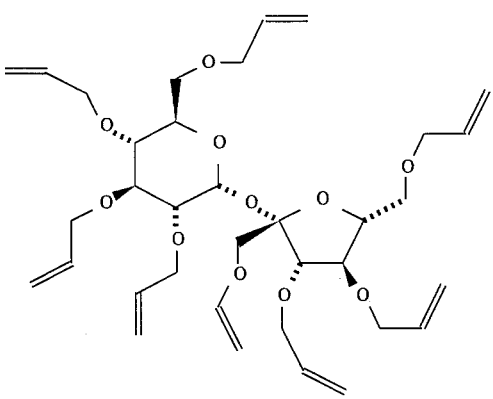

As this allylsucrose derivative has eight double bonds, enough double bonds are available to crosslink many growing polymer chains, resulting in increased crosslinking efficiency. With eight reactive double bonds, octa-O-allylsucrose can crosslink up to eight polymer chains at 100% (theoretical) efficiency. By contrast the commercially available acrylates and methacrylates of, for example, ethyleneglycol, trimethylolpropanetriol and pentaerythritol, can bind only 2 to 4 polymer chains at theoretical efficiency. In this allylsucrose derivative, the allylic double bond is not activated by a neighboring group which could contribute to the stability of the radical generated by the addition of a growing polymer chain radical to the allylic double bond. However, when the polymer chain radical adds across an allylic double bond in octa-O-allylsucrose, the neighboring allylic ethers stabilize the addition by chain transfer of an allylic hydrogen, or the radicals may add monomer and propagate (see FIG. 1.). The resulting allyl radical is then available to engage in intramolecular coupling, crosslinking of another growing methyl methacrylate chain, or initiation of a chain (Peter Munk, *Introduction to Macromolecular Science*, J. Wiley, New York, 1989, pp. 153–154). It has been found that these mechanisms can take place even when the allylsucrose derivative is only partially substituted. This process of stabilization can be seen in FIG. 1.

Enhanced thermal stability also results since during thermal depolymerization at ca. 200° C., radicals formed by polymer chain cleavage can be quenched by hydrogen transfer from unreacted allylic groups on octa-O-allylsucrose. The resulting allyl radicals would then be available to add to other polymer chain radicals to create additional networks, or quench depolymerization.

Figure 1:
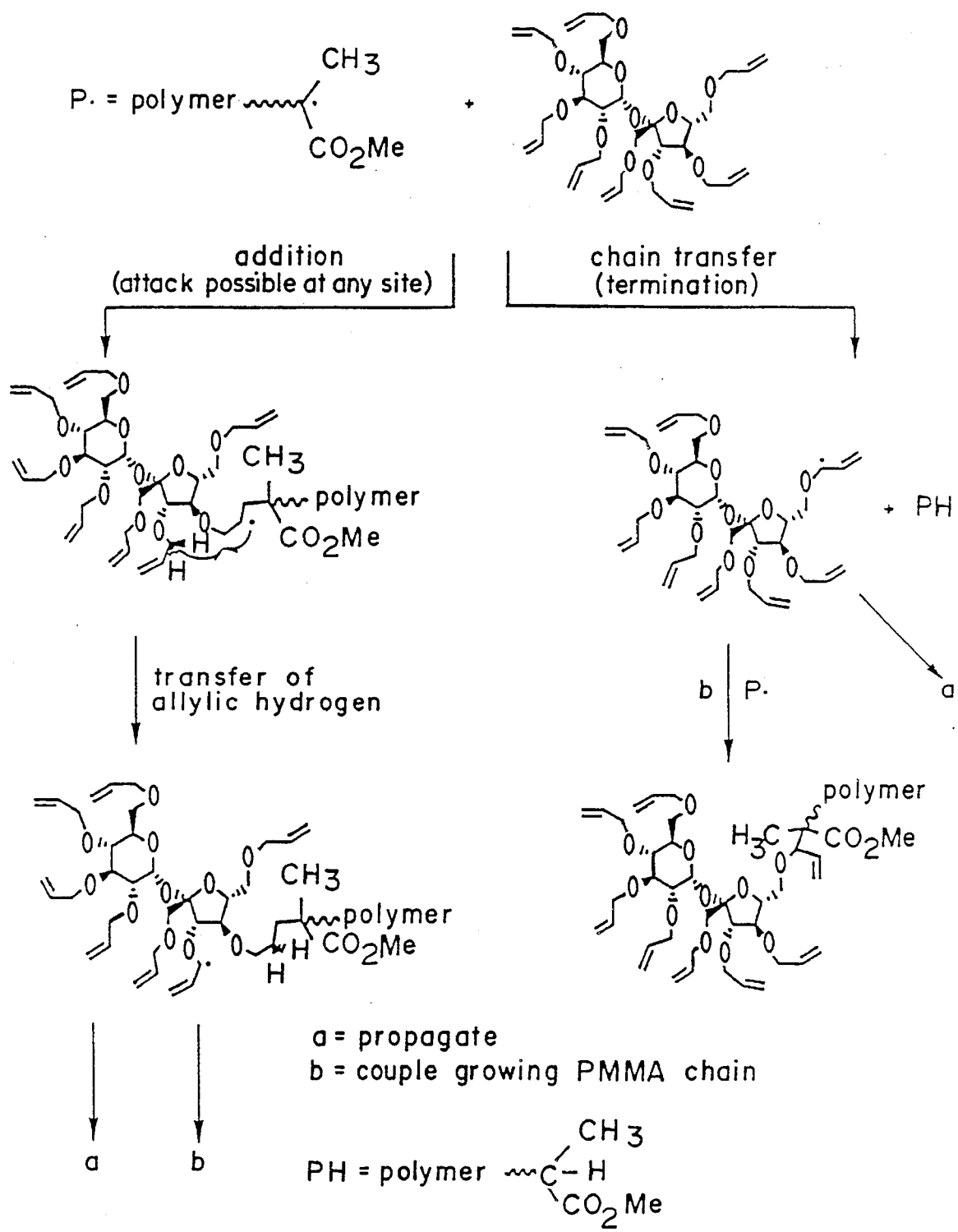
FIG. 1 illustrates the proposed process of stabilization by octa-O-allylsucrose.

1',2,3,3',4,4',6,6'-octa-O-crotylsucrose is a novel non-crosslinking allyl sucrose derivative that is effective in thermal stabilization. It is not a crosslinking agent like octa-O-allylsucrose. However, it may chain transfer and then the resulting radical may propagate, or generate chain branches by coupling of radicals. (FIG. 1 ). This compound and its surprising properties were heretofore unknown. Its structure is as follows:

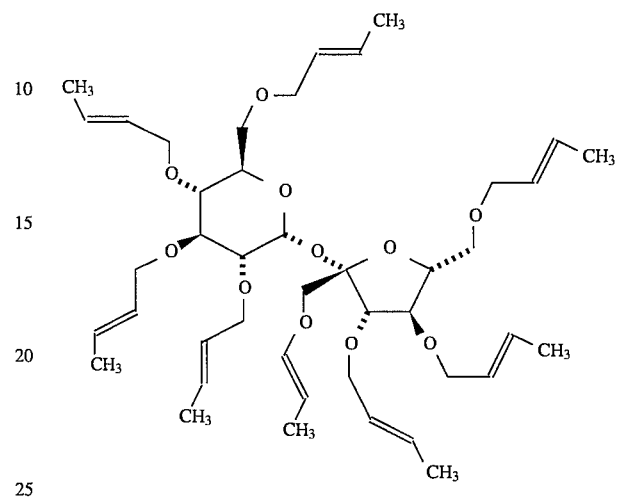

In particular, PMMA's prepared in the presence of octa-O-crotylsucrose are believed to be non-crosslinked, or they may be branched. They are entirely soluble in chloroform. The reduced reactivity of the crotyl group during polymerization with PMMA is believed to be explained by the presence of the terminal electron donating methyl group in the crotyl ether. This methyl group stabilizes the double bond, and sterically diminishes the prospects for the electrophilic methacryl radical to add to it (see, B. Giese et al, *Chem. Ber.*, 116, 3267 (1983)). This rationale is supported by the frontier molecular orbital theory (see, B. Giese, Angew. *Chem. Intl. Ed. English*, 22, 771 (1983)). Since the methacrylate radical is electrophilic, and the crotyl double bond is electron rich, the highest occupied molecular orbital (HOMO) of the crotyl system is suitably placed to interact with the singly occupied molecular orbital (SOMO) of the electrophilic methacryl radical. Simply stated, it is believed that nucleophilic radicals add easily to electron deficient olefins, and electrophilic radicals add easily to electron rich olefins. Since it is believed that in this case this is not happening, as suggested by the fact that PMMA's containing the crotylsucrose are soluble in chloroform, steric factors are preventing addition of the methacryl radical to the crotyl double bond. This is not believed to be the case with PMMA polymers containing octa-O-allylsucrose. Because the terminal double bonds in the allylsucrose are readily accessible, the methacryl radicals add to it to generate a thermoset.

The crotyl ether group, however, may engage in chain transfer reactions at two sites, namely via the methylene between the ether oxygen and the double bond, and the terminal methyl group. This, in turn, may permit the sucrose-based crotyl ether to engage in chain branching by virtue of coupling of radicals. Octa-O-crotylsucrose is present in PMMA polymers as a plasticizer and reduces the Tg to 110° C. Long term thermal stabilities imparted to the thermoplastic by octa-O-crotylsucrose are unprecedented, since PMMA containing one mole % octa-O-crotylsucrose survives thermal aging at 200° C. for 1 and 8.5 days, with only 6 and 22% loss in original mass respectively. Apart from slight yellowing, this polymer does not sag or flow after 24 h at 200° C. in air.

The stabilization agent comprising a sucrose-based monomer having an allyl-containing group on at least one of the hydroxyl groups, preferably a long chain ($C_3$–$C_{20}$) allyl-containing ether group on the hydroxyl group, and more preferably the long chain ($C_3$–$C_{20}$) allyl-containing ether having more than one double bond in the carbon chain, may be synthesized by methods well known to those skilled in the art.

Generally, all monomers were prepared in dry glassware under an inert atmosphere, using conditions described in Sachinvala, N. D. et al., *Carbohydrate Research*, 1991, Vol. 218, pp. 237–245. Proton nuclear magnetic resonance (NMR) spectra were recorded at 500.11 MHz, and carbon-13 NMR spectra were recorded at 125.76 MHz, using a General Electric GN Omega 500 spectrometer. Fast atom bombardment (FAB) mass spectra were obtained on a VG instrument (Model 70 S.E.) using xenon as a bombarding gas. Molecular ions were verified as $[M+1]^+$, $[M+K]^+$ or $[M+Na]^+$ by addition of potassium or sodium iodide to the sample matrix. All organic reagents and solvents (reagent grade, Aldrich Chemical Company) used in monomer syntheses were purified and dried before use according to procedures outlined by Perrin et al (*Purification of Laboratory Chemicals*, 2nd edition, Pergamon Press, Oxford, 1990). Flash column chromatography was performed according to Still et al (*J. Org. Chem.*, 1978, Vol. 43, pp. 2923–2925). Optical rotations were obtained on a Jasco DIP-370 polarimeter at 598 nm. Elemental analyses were performed by Desert Analytics (Tucson, Ariz.).

In particular, the 1',6,6'-trimethacryloyl-2,3,3',4,4'-penta-O-methylsucrose stabilization agent may be synthesized by the method which is described in applicants' commonly assigned patent, U.S. Pat. No. 5,116,961. The disclosure contained therein relating to the synthesis of 1',6,6'-trimethacryloyl-2,3,3',4,4'-penta-O-methylsucrose is hereby incorporated by reference in its entirety.

For the synthesis of 1',2,3,3',4,4',6,6'-octa-O-allylsucrose, the procedure of Brimacombe, J. S. et al (*Carbohydrate Research*, 1966, Vol. 2, pp. 167–169) was modified, and the solvent DMF (because of its hepatotoxicity and incompatibility with sodium hydride at high temperatures) was replaced with DMSO (dimethylsulfoxide) or DMAC (dimethyl acetamide). A dispersion of sodium hydride (60% in oil, 8.4 g, 210 mmol) was washed with dry hexanes (4×15 mL), suspended in DMSO (300 mL), and then treated at 10° C. with a solution of sucrose (5.0 g, 14.62 mmol) in DMSO (30 mL). The temperature of the reaction mixture was monitored internally and allowed to attain 35°–40° C., and the contents stirred for 90 minutes. The resulting yellow mixture was then cooled to 10° C., treated with allyl bromide (13 mL, 150.22 mmol, added over 30 minutes), then allowed to attain a temperature of 40° C. and stirred overnight. Subsequently, the mixture was quenched with 5% aqueous sodium hydroxide (30 mL) at 15° C., diluted with water (500 mL), and extracted with ethylacetate (4×100 mL). The organic extracts were combined, washed with brine (3×150 mL), dried over anhydrous sodium sulfate, filtered, and concentrated in vacuo. Flash column chromatography of the residue on a silica gel (230–400 mesh) column (7 cm×15 cm) using hexanes (2 L), and 10% ethylacetate in hexanes (3 L) provided the desired octa-O-allylsucrose (9.68 g) in 87% yield.

Octa-O-crotylsucrose was prepared in DMAc as well as DMSO (95% yield) using the same procedure as above, except that crotyl chloride was used instead of allyl bromide. Crotyl chloride (98.8%) is predominantly trans, and contains 14% of the cis isomer, and 1.2% 3-chloro-1-butene. Octa-O-crotylsucrose therefore consists of a mixture of cis and trans isomers. Because of this, NMR assignments of the sucrose portion of this compound are without coupling constants, and for the eight crotyl substituents on sucrose, only the ppm ranges of the olefin, methylene and the methyl groups within the crotyl substituents are given. The following characteristics were determined: $^1$H NMR (500 MHz Acetone-$d_6$)δ: 1.60–1.70 (Crotyl methyl protons), 3.165 (H-2), 3.195 (H-4), 3.376 (H-1'b), 3.515 (H-3), 3.536 (2 protons, H-6a, H-6b), 3.565 (H-1'a), 3.587 (H-6'b), 3.689 (H-6'a), 3.825 (H-5'), 3.85–4.30 (crotyl methylene protons), 3.944 (H-5), 3.969 (H-4'), 4.151 (H-3'), 5.428 (H-1), and 5.50–5.78 (crotyl olefinic protons); $^{13}$C NMR (125.76 MHz Acetone-$d_6$) δ17.8–18.0 (crotyl $CH_3$ groups), 69.714 (C-6), 71.5–74.5 (crotyl $CH_2$ groups), 72.091 (C-1'), 72.091 (C-5), 72.402 (C-6'), 78.115 (C-4), 80.181 (C-5'), 80.255 (C-2), 82.025 (C-3), 82.769 (C-4'), 83.703 (C-3'), 90.386 (C-1), 105.035 (C-2'), and 128.0–130.0 (crotyl olefinic CH groups); E.I. mass for $C_{44}H_{70}O_{11}$ calc. 775.00; found $[M-1]^+$=774.

Alternatively, octa-O- and partially-O-crotylated sucroses can be prepared using catalytic amounts of transition metal catalysts. For example, rhodium, ruthenium, iron, cobalt, palladium, iridium, platinum and the like, may be used to complex butadiene and/or isoprene, which is then reacted with sucrose to provide crotyl ethers. Recently, Hill et al showed that the reaction of sucrose with butadiene in the presence of a catalytic amount of palladium (II) acetylacetate succeeded telomerization of the diene and provided mono and dioctadienyl ethers of sucrose (Hill et al, *Tetrahedron Lett.* 35(26):4541 (1994); and Hill et al, German Patent, *Chemical Abstract* 120:301648 (1994)). The problem of telomerization may be avoided, however, if a transition metal catalyst other than palladium is used. More specifically, crotylated sucroses may be prepared as follows. Catalytic amounts of rhodium (III) or other transition metal are dissolved in a DMAc solution of sucrose. Subsequently, the mixture is pressurized with butadiene in a pressure vessel. The contents are stirred under pressure and the progress of the reaction monitored periodically by thin layer chromatography. Upon completion of the reaction (i.e., when the desired number of crotyl groups have been attached to sucrose), the solvent is removed by distillation at 45° C. & 0.01 mm Hg and the residue worked up as known in the art to recover the product in the organic phase. The catalyst is recovered from the aqueous phase by evaporation of water and recrystallization from dilute acid.

Other sucrose-based monomers having an allyl-containing group on at least one of the hydroxyl groups, preferably a long chain ($C_3$–$C_{20}$) allyl-containing ether group on at least one of the hydroxyl groups, and more preferably, the long chain ($C_3$–$C_{20}$) allyl-containing ether having more than one double bond in the carbon chain, may be similarly synthesized by methods well known to those skilled in the art and as generally described above. Depending on the specific structure, these monomers may be crosslinking as with the octa-O-allylsucrose, or not crosslinking, as with the octa-O-crotylsucrose. Thus, both stabilized crosslinked and non-crosslinked polymers may be obtained using these sucrose-based monomers.

These stabilization agents will comprise particular applicability for stabilizing methacrylate esters, acrylate esters, acrylamide and styrene polymers. However, the stabilization agents should also be suitable for stabilizing a variety of polymers which are well known and available in the art.

For example, suitable monomers in the present invention may include methyl methacrylate, methacrylic acid, hydroxyethyl methacrylate, methyl acrylate, acrylic acid, styrene, acrylonitrile, and the like. However, as noted, it is preferred that the monomers used are methacrylate or acrylate esters, such as methyl methacrylate, and acrylamide monomers. Such monomers may be synthesized by methods well known in the art, or may be obtained commercially.

The amount of stabilization agent utilized will comprise those amounts which will result in a polymer having the desired degree of stabilization. Typically, the amount of the stabilization agent utilized will range from about 0.01 to about 50 mole percent, and more preferably, from about 0.1 to about 10 mole percent. However, the particular amount utilized may be varied depending upon the particular monomer or monomers to be polymerized and the desired properties of the resultant polymers.

As previously stated, the subject invention also relates to methods of using non-crosslinking sucrose-based monomers or additives in polymerization processes, and non-crosslinked polymers having enhanced thermal stability obtained using these non-crosslinking sucrose-based additives. The non-crosslinking sucrose-based additive will preferably comprise an alkyl or crotyl-containing ether on at least one of the hydroxyl groups of sucrose. Preferred non-crosslinking sucrose-based additives include octa-O-methylsucrose, and other octa-O-alkylsucroses or partially substituted O-alkylsucroses. Octa-O-methylsucrose, for example, comprises the following structure:

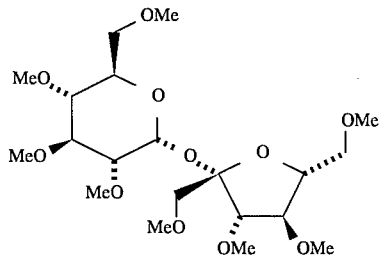

The octa-O-methylsucrose, for example, may be prepared in DMSO or DMAc using the same procedure as described above for octa-O-allylsucrose, except that methyl chloride, methyl bromide, methyl iodide, or dimethylsulfate are used instead of allyl bromide. Preferably, the octa-O-methylsucrose is prepared in DMSO with methyl iodide.

Other octa-O-alkylsucrose monomers may be similarly synthesized using the appropriate alkyl chloride, bromide or iodide as well as by other methods well known to those skilled in the art.

Other non-crosslinking sucrose-based additives may be similarly synthesized by methods well known by those skilled in the art. Some compounds may also be purchased and used as obtained commercially from the manufacturer. For example, sucrose octaacetate® and sucrose diacetate hexaisobutyrate® may be purchased from Eastman Kodak and used as obtained. However, these additives are not effective for stabilization of polymers.

Penta-O-methylsucrose triacetate may be prepared as follows. To a solution of penta-O-methylsucrose (1.0 g, 2.43 mmol) in pyridine (100 mL) at 0° C., acetic anhydride (3 mL, 31.8 mmol) is added and the mixture allowed to stir at room temperature for two days. The volatile contents of the reaction mixture are then removed in vacuo and the residue is reconstituted in ethylacetate and washed successively with 1N HCl, saturated aqueous sodium bicarbonate, water, and brine. The organic layer is then dried over sodium sulfate and concentrated to an oily residue in vacuo. The oily material is then purified by flash column chromatography on silica gel using 50% ethylacetate in hexanes to provide the title compound (1.31 g) in 96% yield.

For example, suitable monomers in the present invention may include methyl methacrylate, methacrylic acid, hydroxyethyl methacrylate, methylacrylate, acrylic acid, styrene, acrylonitrile, and the like. However, as noted, it is preferable that the monomers used are methacrylate or acrylate esters, such as methyl methacrylate, and acrylamide monomers.

The amount of sucrose-based monomer or compound utilized will comprise those amounts which will result in a polymer having the desired properties and degree of non-crosslinked polymerization. Typically, the amount of the non-crosslinking additive utilized will range from about 0.01 to about 50 mole percent, and more preferably from about 0.1 to about 10 mole percent. However, the particular amount utilized may be varied depending upon the particular monomer to be polymerized and the desired properties of the resultant polymers. For example, the non-crosslinking sucrose-based additives or compounds of the present invention may be used as an additive in the polymerization process to result in a polymer having enhanced thermal stability.

The polymerizable mixture of the sucrose-based monomer or compound and the monomer to be polymerized will optionally contain a free radical initiator, which can be a thermal initiator, photo initiator, chemical initiator, or a catalyst to initiate polymerization. However, an initiator or catalyst is not required since polymerization can also be induced by thermal means or by radiation.

The particular initiator or catalyst selected will depend upon the conditions at which the polymerization is to be effected and the desired properties of the resultant polymers. Suitable initiators and catalysts for polymerization processes are well known to those skilled in the art. Such initiators include, for example, alkoxy alkyl benzophenones, acyl peroxides and azobutyronitriles. This list is intended to be exemplary only and other known initiators are within the scope of the present invention.

The actual amount of the initiator or catalyst utilized will typically range from about 0.01 to about 5% by weight, and preferably from about 0.1 to about 3% by weight. However, these amounts will vary dependent upon the particular initiator or catalyst selected, and the conditions of polymerization.

Methods for producing stabilized polymers by the reaction of a monomer and a stabilization and/or crosslinking monomer are well known to those skilled in the art. In the present invention, the particular polymerization conditions will vary dependent upon factors including, e.g., the particular agent used, the particular monomer which is reacted with the agent, the relative proportions thereof, the degree of crosslinking desired (if applicable), the desired molecular weight of the polymer, whether polymerization is effected in bulk or in solution, the particular solvent, the presence of a free radical initiator, and the amount thereof, among other factors. The determination of suitable conditions for polymerization is within the level of skill in the art.

Methods for producing non-crosslinked polymers by the reaction of a monomer and a non-crosslinking sucrose-based monomer or compound are well known to those skilled in the art. In the present invention the particular polymerization conditions will vary dependent upon factors including, e.g., the particular non-crosslinking additive used, the particular monomer which is reacted with the non-crosslinking additive, the relative proportions thereof, the desired molecular weight of the polymer, whether polymerization is effected in bulk or in solution, the particular solvent, the presence of a free radical initiator, and the amount thereof, among other factors. The determination of suitable conditions for polymerization is within the level of skill in the art.

The above-described sucrose derivatives, in particular the allyl and crotyl sucrose derivatives, can be partly converted to allyl glycidyl ethers and then epoxidized to crotyl ethers upon treatment with an acidic or metallic catalyst in the presence of an oxidizing agent. In a preferred embodiment, the sucrose monomer is 1',2,3,3',4,4',6,6'-octa-O-allylsucrose, 1',2,3,3',4,4',6,6'-octa-O-crotylsucrose or 2,3,3',4,4'-penta-O-methylsucrose. For the conversion process, an acidic or metallic catalyst together with an oxidizing agent is added to a monomer comprising an allyl-containing group which is bonded to at least one primary or secondary hydroxyl group on a sucrose, in relative amounts sufficient to produce a sucrose-based epoxy monomer having one to eight epoxy groups per molecule of sucrose. Preferred acidic and metallic catalysts include peracid, molybdenum, tungsten, or vanadium catalysts; more preferred catalysts include peracid and traditional molybdenum, tungsten, and vanadium catalysts; and most preferred catalysts include peracetic acid, molybdenum hexacarbonyl and phospho tungstic acid oligomers. Preferred oxidizing agents include hydrogen peroxide, t-butyl hydroperoxide and derivatives thereof. More preferred oxidizing agents include hydrogen peroxide, t-butyl hydroperoxide, and derivatives thereof.

More specifically, epoxidation may be effected by use of enzymes (lipases) in the presence of a carboxylic acid and hydrogen peroxide. The enzymes oxidize the carboxylic acid to the peroxy acid, which in turn epoxidizes the olefin. A discussion of such enzyme systems may generally be found, for example, in F. Björkling et al, *J. Chem. Soc., Chem. Commun.*, 1990, 1301; E. Santaniello et al, *Chem. Rev.*, 1992, 92, 1071; K. Faber et al, *Synthesis*, 1992, 895; F. Björkling et al, *Tetrahedron*, 1992, 48, 4585; T. Mashino et al, *Tetrahedron Lett.*, 1990 31, 3163; H. Fuet al, *J. Am. Chem. Soc.*, 1991, 113, 5878; and O. Takahashi et al, *Tetrahedron Lett.*, 1989, 30, 1583. These references are hereby incorporated by reference.

Peracids have also been traditionally used to transform olefins to epoxides. Commonly used peracids are peracetic acid, peroxyimidic acids, metachloroperbenzoic acid and magnesium peroxyphthalate. References for various peroxy acids that have been used to effect olefin epoxidation may be found, for example, in *Comprehensive Organic Transformations* (VCH, New York, 1989, pp. 456–459). This reference as well as those cited therein are incorporated by reference.

Tungstic acid reagents may also be employed for epoxidation. Treatment of sodium tungstate with phosphoric acid produces phosphotungstic acid oligomers. These compounds in the presence of excess hydrogen peroxide form peroxy tungstides that readily epoxidize olefins. The reagent is effective even with terminal olefins. Typically, these reactions are performed under phase transfer conditions as described in Fort et al, *Tetrahedron*, 1992, 48, 5099–5110; Venturello et al, *J. Org. Chem.*, 1983, 48, 3831–3833; Quenard et al, *Tetrahedron Lett.*, 1987, 2237–2238; and Prandi et al, *Tetrahedron Lett.*, 1986, 2617–2620. These references are also incorporated by reference.

Other catalysts may also be used to effect epoxidation. For example, in the presence of hydrogen peroxide or alkyl hydroperoxides, tungsten, vanadium and molybdenum compounds catalytically convert olefins to epoxides in non-polar organic solvent or aqueous organic biphases. Such reactions are set forth in, for example, Sharpless et al, *J. Am. Chem. Soc.*, 1973, 95, 6136; Itoh et al, *Chem. Comm.*, 1976, 421–423; Rajan et al, *Tetrahedron*, 1984, 40, 983–990; Antonioletti et al, *J. Org. Chem.*, 1983, 48, 3831–3833; and Mihelich et al, *J. Am. Chem. Soc.*, 1987, 103, 7690–7692).

Depending on the reaction conditions, monomers are isolated which contain from 1 to 8 epoxy groups per sucrose. Preferably, the sucrose-based epoxy monomer is a mixed epoxy-allylsucrose or a mixed epoxy-crotylsucrose. Preferred sucrose-based epoxy monomers include tri-O-(2,3-epoxypropyl)-penta-O-methylsucrose and tri-O-(2,3-epoxybutyl)-penta-O-methylsucrose. Other preferred sucrose-based epoxy monomers of the present invention include triepoxy adducts of the 1',6,6'-tri-O-allyl-, and 1',6,6'-tri-O-crotyl-2,3,3',4,4'-penta-O-methylsucrose monomers, for example, 1',6,6'-tri-O-(2",3"-epoxypropyl)-2,3,3',4,4'-penta-O-methylsucrose and 1',6,6'-tri-O-(2",3"-epoxybutyl)-2,3,3',4,4'-penta-O-methylsucrose monomers. These sucrose-based epoxy compounds may be used, for example, in structural and coatings applications.

Figure 2:
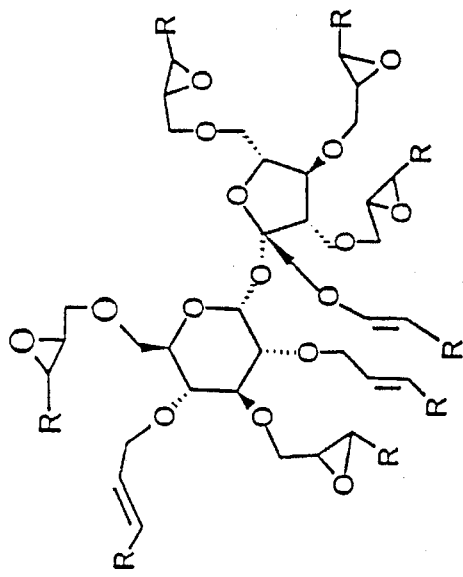
FIG. 2 illustrates sucrose-based epoxy monomers and their precursors.
Figure 2:
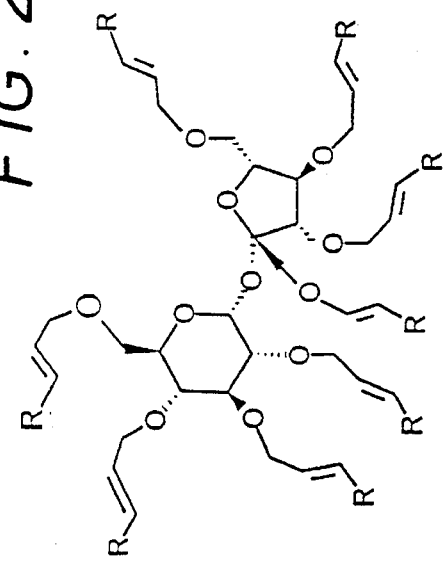
Figure 2:
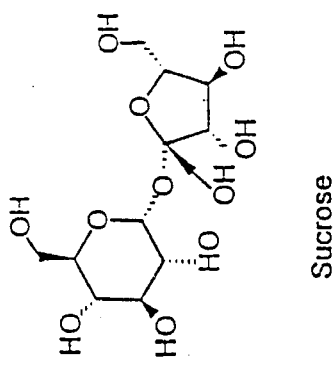
Figure 2:
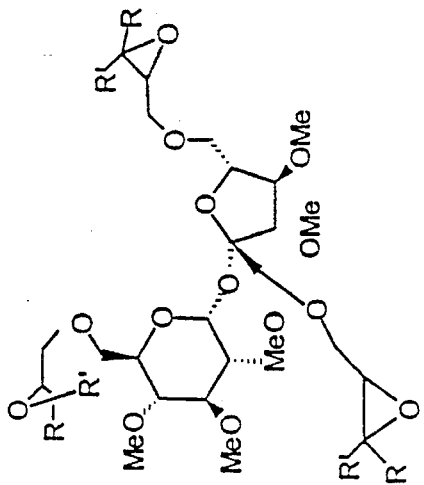
Figure 2:
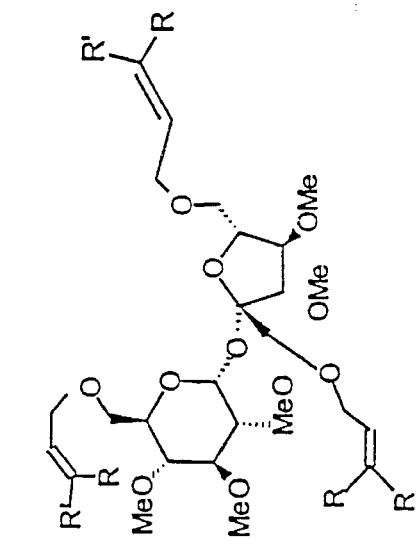

As shown in FIG. 2, octa-O-allylsucrose 2 is epoxidized to produce the mixed allyl-glycidyl derivative 4, wherein the number of epoxy groups per molecule of sucrose is 5. In general, the number of epoxy groups can vary from 1 to 8 per molecule of sucrose. As previously stated, this epoxidation reaction may be achieved, for example, by a variety of acidic or metallic catalysts such as peracids (see, Hudliky, M. *Oxidation in Organic Chemistry*, A.C.S. Monograph 186, American Chemical Society, Washington D.C., 1990, pp 60–64), molybdenum hexacarbonyl (see, Pearson A. J.; Hsu, S. Y., *J. Org. Chem.*, 1986, 51, 2505–2511), and oligmers of phospho tungstic acid (see, Venturello, C.; D'Aloisio, R., *J. Org. Chem.*, 1988, 53, 1553–1557), in the presence of such oxidizing agents as t-butyl hydroperoxide, or hydrogen peroxide.

Similarly, octa-O-crotylsucrose 3, may be converted to the mixed crotyl-2",3"-epoxybutylsucrose derivative 5 by use of acidic and metallic catalysts such as peracids (see, Hudliky, M. *Oxidation in Organic Chemistry*, A.C.S. Monograph 186, American Chemical Society, Washington D.C., 1990, pp 60–64), phospho tungstic acid-derived systems, as well as molybdenum hexacarbonyl. Because the crotyl derivatives contain disubstituted olefins, epoxidation of octa-O-crotylsucrose 3 is more favorable than the epoxidation of octa-O-allylsucrose 2. Despite the fact that numerous other reagents are available for use (see, Larock, R. C. *Comprehensive Organic Transformations*, VCH, FRG, 1989, pp 455–462; Hudliky, M. *Oxidation in Organic Chemistry*, A.C.S. Monograph 186, American Chemical Society, Washington D.C., 1990, pp 60–64), traditional molybdenum, tungsten, and vanadium catalysts are preferred (see, Parshell et al, *Homogeneous Catalysis*, J. Wiley Interscience, New York, 1992, pp 151–153; and McQuillin et al, *Transition Metal Organometallics for Organic Synthesis*, Cambridge University Press, Cambridge, 1991, pp 50–76).

The two step conversion process of sucrose to epoxy monomers produces at least two products. In the first step, octa-O-allylsucrose or octa-O-crotylsucrose is produced. In the second step, octa-O-allylsucrose or octa-O-crotylsucrose is converted to a sucrose based epoxy compound. The resulting epoxy monomers from octa-O-substituted allyl and crotyl sucrose adducts will have 1–8 epoxy groups per sucrose monomer. These monomers may be cured, i.e., crosslinked, to then produce sucrose-based epoxy resins.

A second group of products from the two step conversion of sucrose to epoxy resins are epoxides produced from partially-O-allylated and partially-O-crotylated sucroses. These epoxy products will have different polarities than the fully substituted monomers and should, therefore, find different applications. These epoxies will also be less expensive to produce.

For use in structural and coating applications, for example, the sucrose-based epoxy compounds may be reacted with curing agents generally known in the art to produce a crosslinked resin. Curing agents are coreactants which attack and open the epoxide ring in the crosslinking (curing) process. Curing agents useful in the present invention include both nucleophilic and electrophilic curing agents. Nucleophilic curing agents include ureas, urethanes, amines, thiols, phenols, amides, ketimines, sulfides, mercaptans, acids and imidazoles. (see, Tanaka et al, in *Epoxy Resins: Chemistry and Technology*, 2nd Edition, May, C. A. (editor), Marcel Dekker, New York. 1988, pp 285–463). Examples of amine curing agents include aliamines, polyamines, dicyanodiamide, and aminoplasts (see, Tanaka et al, in *Epoxy Resins: Chemistry and Technology*, 2nd Edition, May, C. A. (editor), Marcel Dekker, New York, 1988, pp 285–463; Mika et al, R. S. *idem,* pp 465–550). Amines, diamines and polyamines are preferred curing agents since each nitrogen to hydrogen bond is potentially capable of reacting with an epoxy group to increase the density of crosslinking. Particularly preferred amines are selected from triethylenetetramine, dicyandiamide and aminoplasts.

Thiols, polysulfides and polymercaptans are also preferred in certain applications for producing fast curing epoxy resins and adhesives. These curing agents attack the epoxide ring at the least hindered site, to open the ring and crosslink (cure) the system. The sulfides and thiols bind metal surfaces and impart excellent adhesive properties to the resins (see, Tanaka et al, in *Epoxy Resins: Chemistry and Technology*, 2nd Edition, May, C. A. (editor), Marcel Dekker, New York, 1988, pp 285–463).

Phenolic and phenoplast resins open the epoxy group in the presence of a strong acid (catalyst) and cure via the hydroxy group at high temperatures. Such curing resins are useful for high temperature applications (see, Tanaka et al, in *Epoxy Resins: Chemistry and Technology*, 2nd Edition, May, C. A. (editor), Marcel Dekker, New York. 1988, pp 285–463).

Acidic curing agents include carboxylic acids and their anhydrides. These curing agents will react with the epoxy group with heating (see, Tanaka et al, in *Epoxy Resins: Chemistry and Technology*, 2nd Edition, May, C. A. (editor), Marcel Dekker, New York, 1988, pp 285–463).

Electrophilic curing agents may also be used. Such curing agents include, e.g., latent acid catalysts, aryl iodonium salts, aryl sulfonium salts and aryl selenium compounds. Latent acid catalysts thermally or photochemically generate acid complexes, promote ring opening and polymerization of the epoxide by acid catalysis. Aryl iodonium and arylsulfonium salts contain stable anions that photochemically release parotic acids. The parotic acids then catalyze epoxy ring opening polymerization, to produce thin coats of epoxy resins on metal surfaces (see, Tanaka et al, in *Epoxy Resins: Chemistry and Technology*, 2nd Edition, May, C. A. (editor), Marcel Dekker, New York, 1988, pp 285–463; Mika, T. F.; Bauer, R. S. *idem,* pp 465–550).

In general, the preferred curing agents include di- and tri-polyamines.

Dynamic mechanical analysis, thermogravimetric testing and analysis and differential scanning calorimetry can be used to establish conditions for curing. These methods are set forth in Epoxy Resins by May (see, Tanaka et al, in *Epoxy Resins: Chemistry and Technology,* 2nd Edition, May, C. A. (editor), Marcel Dekker, New York, 1988, pp 285–463; Mika, T. F.; Bauer, R. S. *idem,* pp 465–550). The description of the preparation of epoxy resins and conditions therefore in these references are hereby incorporated by reference in their entirety.

Figure 3:
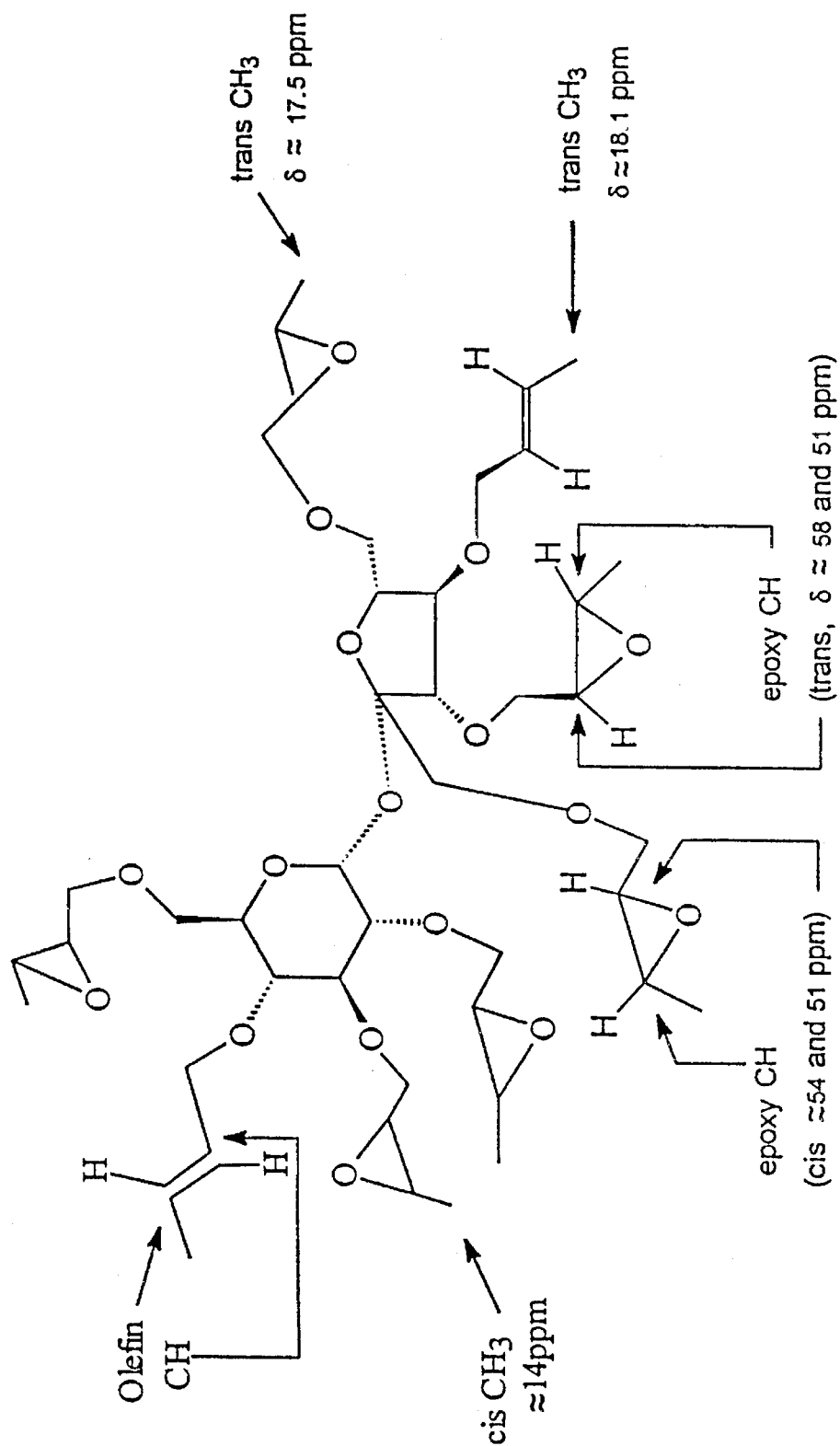
FIG. 3 illustrates the $CH_n$ systems identified in the C-13 spectra of epoxy crotylsucrose.

As previously discussed, the epoxy resins of the present invention may effectively compete with bisphenol-A-based epoxy resins and be used in applications such as paints, coatings, composites and adhesives. Sucrose-based epoxy resins offer several advantages over, for example, bisphenol-A diglycidyl ether, which has previously been used in the art. For example, sucrose-based epoxy resins have higher crosslinking density and versatility. Bisphenol-A diglycidyl ether contains two epoxy groups per molecule. By contrast, sucrose-based resins advantageously can have one to eight epoxy groups per molecule, as desired. In addition, the flexible, unepoxidized allyl and crotyl chains, which are covalently bonded to sucrose (as shown in FIG. 3), act as internal plasticizers within the thermoset and impart flexibility and toughness to the epoxy polymer. Moreover, if polymerization is conducted cationically, the unepoxidized allyl and crotyl groups could react to further increase crosslinking density and Tg.

Sucrose-based epoxy compounds may also be used in applications where urea formaldehyde and phenol formaldehyde resins were previously used, e.g., in wood binding, chip board making, and home insulations. Finding substitutes for urea formaldehyde and phenol formaldehyde resins have become increasingly more important as environmental and health laws regarding the use of formaldehyde, which is a volatile carcinogen, become more stringent. The use of sucrose-based epoxides in such industries is thus particularly advantageous.

The sucrose-based epoxy monomers produced in accordance with the present invention may be characterized, for example, by chromatography, one- and two-dimensional NMR techniques, infrared spectroscopy and mass spectroscopy.

In order to further illustrate the present invention and the advantages thereof, the following specific examples are given, it being understood that the same is intended only as illustrative and in nowise limitative.

EXAMPLES

In order to establish the enhanced thermal stability of the stabilized polymers produced using the sucrose-based monomer containing an allyl-containing group as a stabilizing agent, the present inventors compared the thermal properties, i.e., glass transition temperature and thermal degradation temperature, of polymers produced using the sucrose-based stabilizing agents of the subject invention to the thermal properties of crosslinked polymers produced using conventional crosslinking agents, e.g., trimethyl propane trimethacrylate. The thermal stability of non-crosslinked polymers produced using non-crosslinking sucrose-based additives of the invention were also compared to crosslinked polymers. The thermal degradation was measured graphically by drawing two intersecting tangents continuing from the slopes on the thermal gravimetric analyses (TGA), and their intersection was defined as the onset of catastrophic degradation for a given polymer sample.

In the examples, the copolymers were prepared in glass tubes 50 cm in length, 0.5 cm inside diameter and 2 mm wall thickness. Trimethylolpropane trimethacrylate (TMPTMA technical grade), chlorobenzene and methyl methacrylate (MMA), were purchased from Aldrich Chemical Company and used directly. Additives such as sucrose octaacetate® and sucrose diacetate hexaisobutyrate® were purchased from Eastman Kodak and used as obtained from the manufacturer. All copolymers were prepared in bulk, except copolymers containing one mole percent of either TMPTMA or penta-O-methylsucrose trimethacrylate [$(MAc)_3(OMe)_5$sucrose].

Azobisisobutyronitrile (AIBN, 300 mg) was dissolved in chlorobenzene (110 mL) to give a solution concentration of 2.727 mg/mL. The same quantity of AIBN was used to prepare a solution of AIBN in MMA.

TABLE 1

Quantities of Monomer, Crosslinker and Solvent Used in Copolymer Preparation

| Mole % TMPTMA | mL of Stock Solution (10% TMPTMA in MMA) | mL of Stock Solution (AIBN in MMA 2.727 mg/mL) | mL of Chlorobenzene |
|---|---|---|---|
| 1.00 | 3.38 | 7.30 | 10.68 |
| 0.75 | 2.54 | 8.14 | 10.68 |
| 0.50 | 1.69 | 8.99 | 10.68 |
| 0.25 | 0.85 | 9.83 | 10.68 |
| 0.10 | 0.34 | 10.34 | 10.68 |
| 0.05 | 0.17 | 10.51 | 10.68 |

| Mole % $(MAc)_3(OMe)_5$-sucrose | mL of Stock Solution [10% $(MAc)_3(OMe)_5$-sucrose in MMA] | mL of Stock Solution (AIBN in MMA 2.727 mg/mL) | mL of Chlorobenzene |
|---|---|---|---|
| 1.00 | 6.16 | 4.52 | 10.68 |
| 0.75 | 4.62 | 6.06 | 10.68 |
| 0.50 | 3.08 | 7.60 | 10.68 |
| 0.25 | 1.54 | 9.14 | 10.68 |
| 0.10 | 0.62 | 10.06 | 10.68 |
| 0.05 | 0.31 | 10.37 | 10.68 |

| Mole % Octa-O-allylsucrose | mL of Stock Solution (50% Octa-O-allylsucrose in MMA) | mL of Stock Solution (AIBN in MMA 2.727 mg/mL) | mL of Chlorobenzene |
|---|---|---|---|
| 3.00 | 2.28 | 5.19 | 0 |
| 2.50 | 1.90 | 5.40 | 0 |
| 2.00 | 1.50 | 5.61 | 0 |
| 1.50 | 1.12 | 5.80 | 0 |
| 1.00 | 0.75 | 6.00 | 0 |
| 0.50 | 0.37 | 6.22 | 0 |
| 0.10 | 0.075 | 6.37 | 0 |

EXAMPLE 1

Reagents were mixed to produce crosslinked MMA copolymers containing various mole percentages of TMPTMA, $(MAc)_3(OMe)_5$sucrose and octa-O-allylsucrose. The samples were subsequently diluted with an equal volume of chlorobenzene and the mixtures set to polymerize.

Table 1 shows the amounts (in mL) of stock solutions mixed to achieve the indicated mole percentages of crosslinking agents. The stock solutions used to prepare the polymerization mixtures were as follows:

A ten weight percent stock solution was prepared by mixing TMPTMA (2.9284 g) in MMA (26.355 g, 28.2 mL).

A ten weight percent stock solution was prepared by mixing $(MAc)_3(OMe)_5$sucrose (2.9284 g) in MMA (26.355 g, 28.2 mL).

A fifty weight percent stock solution was prepared by mixing octa-O-allylsucrose (4.25 g) in MMA (4.25 g).

EXAMPLE 2

Reagents were mixed to produce linear MMA copolymers containing one mole percentage of non-crosslinking additive. The non-crosslinking additives mixed with the MMA copolymers included: sucrose octaacetate, sucrose diacetate hexaisobutyrate, octa-O-methylsucrose, penta-O-methylsucrose triacetate and octa-O-crotylsucrose. The polymerization mixtures were prepared using a ten weight percent stock solutions of each additive. Table 2 shows the concentration of each non-crosslinking additive mixed to produce MMA copolymers containing one mole percent of each: sucrose octaacetate, sucrose diacetate hexaisobutyrate, octa-O-methylsucrose, penta-O-methylsucrose triacetate and octa-O-crotylsucrose using the ten weight percent stock solutions of each additive. The non-crosslinking additive was then mixed with the appropriate volumes of MMA to get a final one mole percent concentration.

$$10\% \text{ stock solution} = \frac{1 \text{ g sample}}{1 \text{ g sample} + 9 \text{ g MMA}} = \frac{1 \text{ g sample}}{1 \text{ g} + 9.36 \text{ mL MMA}}$$

The samples were subsequently diluted with an equal volume of chlorobenzene and the mixtures set to polymerize.

TABLE 2

PMMA Containing Non-Crosslinking Additives

| Mole % Additive | mL of Stock Solution (Additive + MMA) | mL of Stock Solution (AIBN in MMA 2.727 mg/mL) | ml of Chlorobenzene |
|---|---|---|---|
| 1 | sucrose octaacetate + MMA stock solution (6.79 mL) | 3.89 | 10.68 |
| 1 | sucrose diacetate hexa-isobutyrate stock solution (8.47 mL) | 2.21 | 10.68 |
| 1 | octa-O-methylsucrose + MMA stock solution (4.54 mL) | 6.14 | 10.68 |
| 1 | penta-O-methylsucrose triacetate + MMA stock solution (5.39 mL) | 5.29 | 10.68 |
| 1 | octa-O-crotylsucrose + MMA stock solution (7.74 mL) | 2.94 | 10.68 |

EXAMPLE 3

The polymer tubes to be used for the polymerization mixtures were silanized by rinsing each tube with a solution of trimethylsilylchloride in methylene chloride (1:1) and subsequently cleaned with methylene chloride (2x), acetone (2x), and deionized water (1x). The tubes were then dried overnight at about 100° C. The polymerization mixtures of Examples 1 and 2, containing monomers, crosslinkers, additives and solvents in amounts as indicated in Tables 1 and 2, were mixed as needed in a one neck flask at room temperature, and purged for 2 to 3 minutes with helium gas. The mixture was then transferred via a teflon coated syringe containing a teflon needle to two polymerization tubes and filled to the 30 cm mark. The contents of the polymerization tubes were degassed by the freeze thaw method in vacuo (4 cycles), sealed with a propane gas torch and allowed to polymerize in a water bath at about the following temperatures and time regimens: 25° C., 2 days; 35° C., 2 days; 45° C., 1 day; 55° C., 1 day; 65° C., 1 day; 70° C., 1 day. The polymer samples were then removed from the tubes, cut into 1 cm cylinders and stored in airtight amber bottles.

EXAMPLE 4

For the conversion of allyl and crotyl sucroses to their respective allyl-glycidyl and epoxyocrotyl adducts, several different reaction conditions were studied and analyzed.

Preparation of a mixture of epoxy allyl sucroses using tungstic acid catalysis The procedure of Cabere, P. et al *Tetrahedron*, 1992, 48, 5099, was modified. To an aqueous solution containing 20% $H_2O_2$ (1.74 mL 30% $H_2O_2$ plus 0.25 mL water), and sodium tungstate dihydrate (0.165 g, 0.5 mmol) was added phosphoric acid (85% by weight in water, 0.098 g, 0.85 mmol) and then 10% aqueous sodium hydroxide (dropwise) to adjust the pH of the solution to 1.9. The mixture was stirred in an oil bath maintained at 40° C. and treated with octa-O-allylsucrose (0.828 g, 1.25 mmol, 10 mmols of allyl groups) dissolved in methylene chloride (15 mL) and Aliquot 336 (Aldrich Chemical Company, 3.2 mmol). The reaction was vigorously stirred at 40° C. for 24 hours and monitored by thin layer chromatography using 10% acetone in hexanes ($R_f$ octa-O-allyl sucrose 0.61). After 24 hours the reaction mixture was treated with additional hydrogen peroxide (20% 1 mL) and stirred for 24 hours. After 2 days, the reaction was quenched by addition to a solution of 0.1N ferrous sulfate (10 mL) at 0° C. and extracted with methylene chloride (3×20 mL). The combined organic layers were washed with water (2×20 mL) then brine (20 mL), then dried over anhydrous magnesium sulfate, and then concentrated in vacuo. Column chromatography of the oil on silica gel (230–240 mesh, 4×15 cm) using 500 mL each of 10% acetone in hexanes, 20% acetone in hexanes, 30% acetone in hexanes and 40% acetone in hexanes provided the following mixture of products: octa-O-allylsucrose (120 mg, 0.18 mmol); epoxy allyl sucroses with an average of 2 epoxy groups/sucrose ($R_f$ 0.24, 140 mg, 0.20 mmol); epoxy allyl sucroses with an average of 3 epoxy groups/sucrose ($R_f$ 0.14, 200 mg, 0.28 mmol); epoxyalkyl sucrose with an average of 4 epoxy groups/sucrose ($R_f$ 0.11; 220 mg, 0.30 mmol). The recovery of products was 78.6% [(0.18+0.20+0.28+0.30)mmol/1.25 mmol].

NMR Method for Determining the Epoxy Groups in Epoxy-Allylsucrose Mixtures

A representative sample from the column chromatography discussed above was dried in vacuo (0.1 mm Hg, 35° C. overnight), dissolved in 0.5 mL of deuterated acetone (acetone $D_6$), and then placed in an NMR tube and subjected to $^{13}$C-NMR spectroscopy (125.76 MHz). Spectra were recorded under the following instrument conditions: pulse with 10 µs; pulse delay 1 second; acquisition time 0.68 sec; spectral width 2.5000 Hz, offset 14488.16 Hz; dwell time 40 µsec. Since the relaxation times (T) of all carbon-13 nuclei bearing one or more hydrogens (CH, $CH_2$, or $CH_3$) in the molecule were determined to be 0.3±0.05 sec., the 1 sec. pulse delay gave the nuclei ample time to establish magnetic equilibrium. This enabled the C-13 signals to be integrated without the influence of transferred nuclear Overhauser effects from the attached protons. For the epoxy allylsucroses, the epoxy methylene ($CH_2$) resonances appeared at about 45 ppm, and the epoxy methine (CH) resonances appeared at about 51 ppm. Correspondingly, the vinyl methylene ($CH_2$) and vinyl methine resonances for the allyl groups in the same compound appeared at 116 and 135 ppm, respectively.

Table 3 shows the positions and the integral values of the four $CH_n$ systems for a sample containing three epoxy groups per sucrose.

TABLE 3

| Type of $CH_n$ System | position (ppm) | $^{13}$C integral value |
|---|---|---|
| epoxy $CH_2$ system | ≈45 ppm | 25.966 |
| epoxy CH system | ≈51 ppm | 24.858 |
| allyl $CH_2$ system | ≈116 ppm | 43.008 |
| allyl CH system | ≈135 ppm | 39.807 |

The percent epoxidation may be calculated by the formula $$\% \text{ epoxidation} = \frac{\text{Integral epoxy CH}}{\text{Integral epoxy CH} + \text{integral allyl CH}} \times 100$$

$$= [(24.8582/24.858 + 39.807)] \times 100$$

$$= 38.43\% \text{ epoxidation}$$

Therefore the number of epoxy group per sucrose may be determined by 0.3843×8 possible positions that could be epoxidized, i.e., 3.07 epoxy groups per sucrose.

Preparation of Epoxy Allylsucroses by the Peracetic Acid Method

To a methylene chloride solution (4 ml) of octa-O-allylsucrose (331 mg, 0.5 mmol) was added sodium acetate (328 mg, 4.0 mmol) and the contents were cooled to 15° C. in an ice bath. To this suspension was added aqueous peracetic acid (32%, 840 μL, 4 mmol), the contents allowed to equilibriate to 40° C. and the progress of the epoxidation monitored hourly by thin layer chromatography. After 24 hours, to the reaction mixture were added water (8 ml, to dissolve sodium acetate and acetic acid and 0.114 ferrous sulfate (5 mL, to destroy excess peroxide). The contents were then transferred to a separatory funnel and the organic layer separated.

The aqueous layer was then extracted with methylene chloride (4×10 mL) and all the organic layers were combined. The combined organic extracts were serially washed with 5% aqueous sodium hydroxide and then with water (2×5 mL each), then dried over anhydrous magnesium sulfate and concentrated in vacuo. The average number of epoxy group per sucrose were determined by the NMR method discussed above and found to be about 5.2 groups per sucrose.

Preparation of Epoxy Crotylsucroses by the Peracetic Acid Method

To a methylene chloride solution (16 mL) of octa-O-crotyl-sucrose (1.55 g, 2.0 mmol) was added sodium acetate (1.312 g, 16 mmol). To this vigorously stirring suspension was added aqueous peracetic acid (32%, 3.36 mL, 16 mmol) and the mixture stirred for 24 hours, at which time no octa-O-crotylsucrose could be observed by TLC. The mixture was then treated with water (8 mL) and iron (II) sulfate 0.1N (2×5 mL), and the organic layer separated. The aqueous layer was further extracted with methylene chloride (4×15 mL), and the organic layers were combined, washed serially with aqueous sodium hydroxide (5% solution, 2×5 mL), water (2×5 mL) and brine (10 mL), dried over anhydrous magnesium sulfate and then evaporated. The resulting oil weighed 1.774 g (96.25% yield).

Figure 4C:
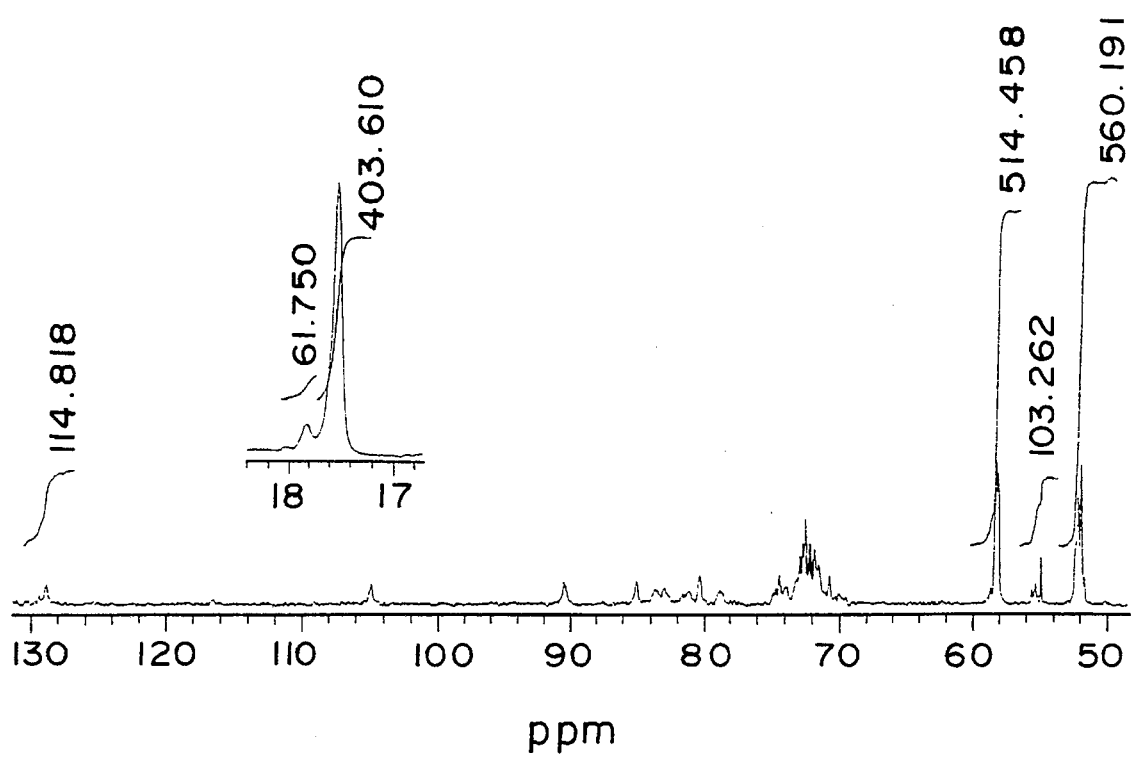
FIG. 4 shows mass spectra of epoxy crotyl sucroses with varying degrees of expoxidation.

NMR Method for determining the number of Epoxy groups in samples of mixtures of Epoxy-crotylsucroses FIG. 3 shows the $CH_n$ systems identified in the C-13 spectra of epoxy crotylsucroses that may be used to determine the degree of epoxidation of crotylated sucroses. These are the cis and trans crotyl $CH_3$ groups ($\delta$=14 and 18 ppm, respectively), the cis and trans epoxy crotyl $CH_3$ groups ($\delta$=17.5 ppm); the cis and trans epoxy CH groups (at $\delta$=51, 55 and 58 ppm); and the olefin CH absorptions at 128 ppm. FIG. 4 shows carbon-13 NMR spectra of epoxy crotyl sucroses with varying degrees of epoxidation. FIGS. 5–11 show mass spectral data confirming the presence of epoxy crotyl sucroses containing 2 to 8 epoxy groups per sucrose.

Percent epoxidation in epoxy crotyl sucroses may be determined by dividing the sum of the epoxy CH integrals by the sum of the epoxy CH integrals and olefin CH integrals and multiplying by 100.

% epoxidation =

$$\frac{\text{epoxy CH integral values}}{\text{epoxy CH integral values} + \text{olefin CH integral values}} \times 100$$

The number of epoxy groups per sucrose may then be calculated by multiplying the % epoxidation number by 8, i.e., Number of epoxy/sucrose=% epoxidation×8.

EXAMPLE ≡

Reaction of Sucrose-Based Epoxy Resins with Amine Curing Agents and the Bonding of Aluminum, Glass, Steel and Wood Strips.

The sucrose based epoxy resins prepared above were tested for their ability to: (a) react with amine curing agents, and (b) bind two strips of aluminum, glass, steel and wood when cured on those surfaces.

Molar equivalent amounts of the sucrose-derived epoxy resin, containing seven epoxy groups per sucrose, and diethylene triamine were mixed to form a clear colorless paste. The mixture was then applied to both sides of aluminum (½ inch×2 inches), glass (microscope slides), steel (½ inch×2 inches), and wood (tongue depressors) strips. The paste was spread about 1 mm thick, over a one inch length on the strips, and spanned the width of the strips. The coated sides were then overlapped (lap jointed) and held together by binder clips. The lap-jointed strips were then placed in a vacuum oven at 90° C. (10 mm Hg) and cured over night (12 hours) at that temperature and pressure, and then allowed to equilibriate to ambient conditions.

The cured lap-jointed strips could not be pulled apart by pulling with pliers along the shear plane. The lap-jointed glass microscope slides were not tested with pliers.

All of the references cited in the specification are hereby incorporated by reference to the same extent as if each of the references was individually incorporated by reference.

Other embodiments of the invention will be apparent to those skilled in the art from consideration of the specification and practice of the invention disclosed herein. It is intended that the specification and examples be considered as exemplary only, with the true scope and spirit of the invention being indicated by the following claims.

We claim:

1. A method for producing a saccharide-based epoxy monomer having one to eight epoxy groups per molecule of saccharide, which comprises reacting a mixture comprising:

(a) a monomer comprising an allyl-containing group which is bonded to at least one primary or secondary hydroxyl group on a saccharide, and (b) an acidic or metallic catalyst in the presence of an oxidizing agent, in relative amounts sufficient to produce a saccharide-based epoxy monomer having one to seven epoxy groups per molecule of saccharide.

2. The method of claim 1, wherein the allyl-containing group is an allyl-containing ether comprising from about 3 to 20 carbon atoms.

3. The method of claim 2, wherein the allyl-containing ether comprises an allyl group having unsaturation beta to the ether group.

4. The method of claim 3, wherein the acidic or metallic catalyst is a peracid, molybdenum, tungsten, or vanadium catalyst.

5. The method of claim 1, wherein the acidic or metallic catalyst is a peracid, molybdenum, tungsten, or vanadium catalyst.

6. The method of claim 5, wherein the acidic or metallic catalyst is a peracetic acid, molybdenum hexacarbonyl, or phospho tungstic acid oligomer catalyst.

7. The method of claim 1, wherein the oxidizing agent comprises hydrogen peroxide, t-butyl hydroperoxide, cumene hydroperoxide, meta-chloroperoxy benzoic acid, or peracetic acid.

8. The method of claim 7, wherein the oxidizing agent is hydrogen peroxide or t-butyl hydroperoxide.

9. The monomer produced by the method of claim 1.

10. A method for producing sucrose-based epoxy monomers having one to eight epoxy groups per molecule of sucrose, which comprises reacting a mixture comprising:

(a) a sucrose monomer having an allyl-containing group on at least one of the hydroxyl groups; and (b) an acidic or metallic catalyst in the presence of an oxidizing agent, in relative amounts sufficient to produce a sucrose-based epoxy monomer.

11. The method of claim 10, wherein the allyl-containing group of the sucrose monomer is a $C_3$–$C_{20}$ allyl-containing ether.

12. The method of claim 11, wherein the allyl-containing group is a $C_3$–$C_{20}$ allyl-containing ether which comprises more than one double bond.

13. The method of claim 10, wherein the sucrose monomer is 1',2,3,3',4,4',6,6'-octa-O-allylsucrose, 1',2,3,3',4,4',6,6'-octa-O-crotylsucrose, 1',6,6'-tri-O-crotyl-2,3,3',4,4'-penta-O-methylsucrose or 1',6,6'-tri-O-allyl-2,3,3',4,4'-penta-O-methylsucrose.

14. The method of claim 13, wherein triepoxy adducts of the 1',6,6'-tri-O-allyl-, or 1',6,6'-tri-O-crotyl-2,3,3',4,4'-penta-O-methylsucrose monomers are produced.

15. The method of claim 14, wherein the triepoxy adduct produced is 1',6,6'-tri-O-(2",3"-epoxypropyl)-2,3,3',4,4'-penta-O-methylsucrose and 1',6,6'-tri-O-(2",3"-epoxybutyl)-2,3,3',4,4'-penta-O-methylsucrose monomer.

16. The method of claim 15, wherein the acidic or metallic catalyst is a peracid, molybdenum, tungsten, vanadium, or titanium catalyst.

17. The method of claim 10, wherein the acidic or metallic catalyst is a peracid, molybdenum, tungsten, or vanadium catalyst.

18. The method of claim 17, wherein the acidic or metallic catalyst is a peracetic acid, molybdenum hexacarbonyl, or tungstic acid oligomercatalyst.

19. The method of claim 10, wherein the oxidizing agent comprises hydrogen peroxide, t-butyl hydroperoxide, cumene hydroperoxide, metachloroperoxy benzoic acid, or peracetic acid.

20. The method of claim 19, wherein the oxidizing agent is hydrogen peroxide or t-butyl hydroperoxide.

21. The monomer produced by the method of claim 10.

22. A method for preparing an epoxy-allylsucrose or epoxy-crotylsucrose monomer comprising:

(a) treating sucrose with a suspension of dimethylsulfoxide and sodium hydride at a temperature of between about 0° and about 10° C. to obtain a sucrose mixture;

(b) stirring the sucrose mixture for between about 30 and about 80 minutes while allowing the temperature to attain between about 35° to about 40° C.;

(c) cooling the sucrose mixture to between about 0° and about 10° C.;

(d) treating the sucrose mixture with allyl or crotyl chloride;

(e) stirring the mixture from (d) for a time sufficient for the sucrose to react with the allyl or crotyl chloride;

(f) recovering octa-O-allylsucrose or octa-O-crotylsucrose;

(g) adding an acidic or metallic catalyst in the presence of an oxidizing agent to the octa-O-allylsucrose or octa-O-crotylsucrose in relative amounts sufficient to produce an epoxy-allylsucrose or epoxy-crotylsucrose monomer; and (h) recovering the epoxy-allylsucrose or epoxy-crotylsucrose monomer.

23. The epoxy-allylsucrose or epoxy-crotylsucrose monomer produced by the method of claim 22.

* * * * *

UNITED STATES PATENT AND TRADEMARK OFFICE
CERTIFICATE OF CORRECTION

PATENT NO.      :   5,571,907

DATED           :   November 5, 1996

INVENTOR(S)     :   Navzer D. SACHINVALA et al.

It is certified that error appears in the above-identified patent and that said Letters Patent is hereby corrected as shown below:

On the title page: [19] & [75]
please delete "Sachinala et al." and insert therefor --Sachinvala et al.--.

Signed and Sealed this

Seventh Day of January, 1997

*Attest:*

BRUCE LEHMAN

*Attesting Officer*    Commissioner of Patents and Trademarks